United States Patent [19]

Franzmann et al.

[11] Patent Number: 5,679,694
[45] Date of Patent: Oct. 21, 1997

[54] TETRACYCLIC COMPOUNDS, INTERMEDIATES FOR THEIR PREPARATION AND THEIR USE AS ANTITUMOR AGENTS

[75] Inventors: Karl Witold Franzmann; Jeremy Nigel Stables, both of Beckenham; Patrick Vivian Richard Shannon, Penarth; Nagaraja Kodanda Ranganatha Rao, Birchgrove, all of Great Britain; Laddawan Chunchatprasert, Khon Kaen, Thailand

[73] Assignees: The Wellcome Foundation Ltd.; University College Cardiff Consultants Limited, both of United Kingdom

[21] Appl. No.: 743,283

[22] Filed: Nov. 4, 1996

Related U.S. Application Data

[63] Continuation of Ser. No. 373,285, filed as PCT/GB93/01512, Jul 19, 1993 published as WO94/02483, Feb. 3, 1994, abandoned.

[30] Foreign Application Priority Data

Jul. 20, 1992 [GB] United Kingdom ............ 9215361

[51] Int. Cl.$^6$ .................. A61K 31/40; C07D 403/06
[52] U.S. Cl. .................. 514/339; 514/410; 514/443; 546/272; 548/421; 548/468; 549/42
[58] Field of Search ................... 514/339, 410, 514/443; 548/421, 468; 549/42; 546/272

[56] References Cited

PUBLICATIONS

Khoshtariya et al, Khim. Get. Soed, 10, 1366–1370, (Oct. 1984) Indolobenzo[b]Furans 2.* Some Indolo[5,6–d]–and Indolo[5,4–d] benzo[b]furans.
Khoshtariya et al Khim. Get. Soed., 3,355–358, (Mar. 1985) Indolobenzofurans 1. Synthesis of isomeric Indolobenzo[b] Furans.
27–Heterocycles vol. 107, 1987 p. 569–107:217417d.
Chemical Abstracts vol. 102, 1985 p. 584–102:220773u.
Chemical Abstracts vol. 95, 1981 p. 638–95:97622b.
22–Physical Org. Chem. vol. 104, 1986 p. 625–104:148142j.
Chemical Abstracts vol. 98 1983 p. 534–98:89114j.
Chemical Abstracts vol. 93, 1980 p. 914–93:46472d.
Chunchatprasert, L. et al., J. Chem. Soc. Perkin Trans. I, pp. 1779–1783, No. 14, Jul. 21, 1992.

*Primary Examiner*—Jacqueline Haley
*Attorney, Agent, or Firm*—Nixon & Vanderhye

[57] ABSTRACT

The invention relates to compounds of formula (I) which have been found to possess anti-tumor activity. Pharmaceutical compositions and methods of treating tumors are also disclosed.

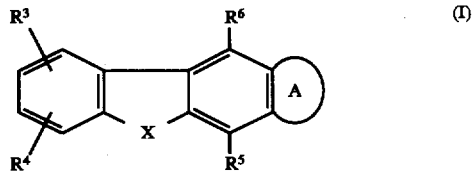

7 Claims, No Drawings

TETRACYCLIC COMPOUNDS, INTERMEDIATES FOR THEIR PREPARATION AND THEIR USE AS ANTITUMOR AGENTS

This is a continuation of U.S. Ser. No. 08/373,285 filed Jan. 31, 1995, now abandoned, which is a National Stage application of PCT/GB93/01512 filed Jul. 19, 1993 and published as WO94/02483 on Feb. 3, 1994.

The present invention relates to heterocyclic compounds which have been found to have anti-tumor activity. More specifically, the invention concerns Pyrrolo [3,2-b] carbazoles, 1H-Benzofuro [3,2-f] indoles and 1H-[1] Benzothieno [2,3-f] indoles, methods for their preparation, pharmaceutical formulations containing them and their use as anti-tumor agents.

Research in the area of cancer chemotherapy has produced a variety of anti-tumor agents, which have differing degrees of efficacy. Standard clinically used agents include adriamycin, antinomycin D, methotrexate, 5-fluorouracil, cis-platinum, vincristine and vinblastine. However, these presently available anti-tumor agents are known to have various disadvantages, such as toxicity to healthy cells and resistance to certain tumor types.

There thus exists a continuing need to develop new and improved anti-tumor agents.

Khoshtariya et al, khim. Geterotsikl. Soedin (1980), (2) 203-8, disclose the synthesis of certain indolobenzo[b]thiophenes.

Khoshtariya et al, khim Geterotsikl Soedin (1984), (10) 1366-70, disclose the synthesis of certain indolobenzo[b]furans.

Kakhabrishvili et al, khim Geterotsikl Soedin (1985), (3) 355-8 disclose the synthesis of certain derivatives of indolo [5,6-d] and indolo [5,4-d] benzo[b] furans.

The patent specification EP447,703 discloses the synthesis of certain benzo(5,6-b)benzofuran-2-carboxylates.

There have now been discovered novel compounds which exhibit anti-tumor cell activity with low toxicity against normal cell lines.

Thus, a first aspect of the present invention provides a compound of the general formula (1)

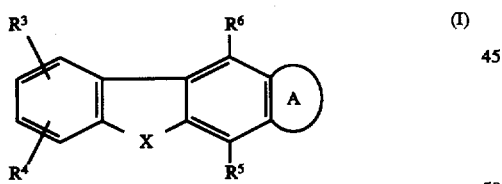

and salts and physiologically functional derivatives thereof, wherein A is

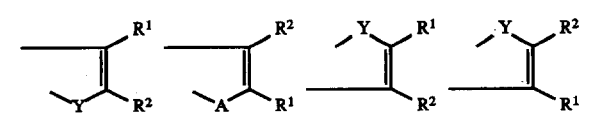

X is O, S, SO, $SO_2$, $CH_2$, CO or $NR^7$, wherein $R^7$ is H, $C_{1-10}$ alkyl, aralkyl containing 1 to 4 carbon atoms in the alkyl portion and up to 10 carbon atoms in the aryl portion, aryl containing up to 10 carbon atoms, alkenyl, $C_{1-10}$ acyl, alkynyl, or sulphonyl optionally substituted by $C_{1-10}$ alkyl, aryl containing up to 10 carbon atoms or aralkyl containing 1 to 4 carbon atoms in the alkyl portion and up to 10 Carbon atoms in the aryl portion;

Y is O, S, SO, $SO_2$, $CH_2$, CO or $NR^7$;

$R^1$ is $COR^8$, $COOR^8$, CHO, $CH_2OH$, $CH_2OR^9$, $CONH_2$, $CONHNR^{10}R^{11}$, $CONHR^{10}$, $CONR^{10}R^{11}$, $COO(CH_2)_nNR^{10}R^{11}$, wherein $R^8$ is H, $C_{1-10}$ alkyl, aryl containing up to 10 carbon atoms and optionally substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano, or aralkyl containing 1 to 4 carbon atoms in the alkyl portion and up to 10 carbon atoms in the aryl portion, $R^9$ is $C_{1-10}$ acyl optionally substituted by $C_{1-10}$ alkyl, $C_{1-10}$ alkoxy, halo, sulphonyl, amino (optionally substituted by one or two $C_{1-10}$ alkyl groups), haloalkyl, sulphinyl or cyano, $R^{10}$ and $R^{11}$ are independently hydrogen, $C_{1-10}$ alkyl or aryl containing up to 10 carbon atoms, and n is 1 to 4 carbon atoms;

$R^2$ is H, $COOR^8$, $C_{1-10}$ alkyl, aryl containing up to 10 carbon atoms, optionally substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano, or $CH_2CH_2CO_2R^{12}$ wherein $R^{12}$ is $C_{1-10}$ alkyl or aryl containing up to 10 carbon atoms;

$R^3$ and $R^4$ are independently H, hydroxy, $C_{1-10}$ alkyl, haloalkyl, $C_{1-10}$ alkoxy, halo, cyano, nitro, amino, alkylamino, dialkylamino, alkyl substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano, carboxyl or $CO_2R^{12}$;

$R^5$ is H, $C_{1-10}$ alkyl, optionally substituted by $C_{1-10}$ alkyl $C_{1-10}$ alkoxy, halo, sulphinyl, amino (optionally substituted by one or two alkyl groups), haloalkyl, sulphonyl or cyano, aralkyl containing 1 to 4 carbon atoms in the alkyl portion and up to 10 carbon atoms in the aryl portion, nitro, amino, halo, cyano, CHO, $COOR^8$;

$R^6$ is H, aryl containing up to 10 carbon atoms, $C_{1-10}$ alkyl, aralkyl containing 1 to 4 carbon atoms in the alkyl portion and up to 10 carbon atoms in the aryl portion, nitro, halogen, CHO or $COR^{13}$ wherein $R^{13}$ is $C_{1-10}$ alkyl or aryl containing up to 10 carbon atoms;

with the proviso that (i) when $R^2$, $R^3$, $R^4$, $R^5$ and $R^6$ are all H and A is

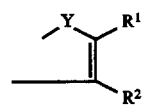

wherein Y is NH and X is O or S, then $R^1$ is not $CO_2H$ or $CO_2Et$; and (i) when $R^2$, $R^3$, $R^4$, $R^5$ and $R^6$ are all H and A is

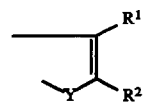

wherein Y is NH, and X is O then $R^1$ is not CHO; and (iii) Y is not O when X is O.

In yet a further aspect of the present invention provides a compound of the general formula (1) above, wherein A is

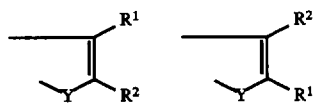

-continued

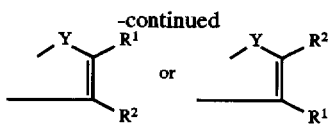

X is O, S, SO, SO$_2$, CH$_2$, CO or NR$^7$, wherein R$^7$ is H, C$_{1-10}$ alkyl, aralkyl containing 1 to 4 carbon atoms in the alkyl portion and up to 10 carbon atoms in the aryl portion, aryl containing up to 10 carbon atoms, alkenyl, C$_{1-10}$ acyl, akynyl or sulphonyl;

Y is O, S, SO, SO$_2$, CH$_2$, CO or NR$^7$;

R$^1$ is COOR$^8$, CHO, CH$_2$OH, CH$_2$OR$^9$, CONH$_2$, CONHR$^{10}$ or CONR$^{10}$R$^{11}$, wherein R$^8$ is H, C$_{1-10}$ alkyl, aryl containing up to 10 carbon atoms, optionally substituted by C$_{1-10}$ alkyl, C$_{1-10}$ alkoxy, halo, sulphinyl, amino (optionally substituted by one or two C$_{1-10}$ alkyl groups), haloalkyl, sulphonyl or cyano or aralkyl Containing 1 to 4 carbon atoms in the alkyl portion and up to 10 carbon atoms in the aryl portion, R$^9$ is C$_{1-10}$ acyl optionally substituted by C$_{1-10}$ alkyl, C$_{1-10}$ alkoxy, halo, sulphinyl, amino (optionally substituted by one or two C$_{1-10}$ alkyl groups), haloalkyl, sulphinyl or cyano, and R$^{10}$ and R$^{11}$ are independently C$_{1-10}$ alkyl or aryl containing up to 10 carbon atoms;

R$^2$ is H, COOR$^8$, C$_{1-10}$ alkyl, aryl containing up to 10 carbon atoms, optionally substituted by C$_{1-10}$ alkyl, C$_{1-10}$ alkoxy, halo, sulphinyl, amino (optionally substituted by one or two C$_{1-10}$ alkyl groups), haloalkyl, sulphonyl or cyano or CH$_2$CH$_2$CO$_2$R$^{12}$ wherein R$^{12}$ is C$_{1-10}$ alkyl or aryl containing up to 10 carbon atoms;

R$^3$ and R$^4$ are independently H, hydroxy, C$_{1-10}$ alkyl, haloalkyl, C$_{1-10}$ alkoxy, halo, cyano, nitro, amino, alkylamine, dialkylamino, alkyl substituted by C$_{1-10}$ alkyl, C$_{1-10}$ alkoxy, halo, sulphinyl, amino (optionally substituted by one or two C$_{1-10}$ alkyl groups), haloalkyl, sulphonyl or cyano, carboxyl or CO$_2$R$^{12}$;

R$^5$ is H, C$_{1-10}$ alkyl, optionally substituted by C$_{1-10}$ alkyl, C$_{1-10}$ alkoxy, halo, sulphinyl, amino (optionally substituted by one or two C$_{1-10}$ alkyl groups), haloalkyl, sulphonyl or cyano, aralkyl containing 1 to 4 carbon atoms in the alkyl portion and up to 10 carbon atoms in the aryl portion, nitro, halo, cyano CHO;

R$^6$ is H, C$_{1-10}$ alkyl, aralkyl containing 1 to 4 carbon atoms in the alkyl portion and up to 10 carbon atoms in the aryl portion, nitro, halo, CHO or COR$^{13}$ wherein R$^{13}$ is C$_{1-10}$ alkyl or aryl containing up to 10 carbon atoms with the proviso described above.

Alkyl groups present in general formula (I) may be straight or branched chain alkyl groups, and suitably contain 1–6 carbon atoms. Examples of such alkyl groups include methyl, ethyl, t-butyl and the like.

Acyl group may be straight or branched and suitable contain 1–6 carbon atoms. Examples of suitable acyl groups include ethanoyl and propanoyl groups.

Alkoxy may be straight or branched and suitably contain 1–6 carbon atoms. Examples of suitable alkoxy groups include methoxy, ethoxy and the like.

Aryl includes Both carbocyclic acyl groups and heterocyclic aryl groups. Carbocyclic aryl group include, e.g. phenyl and naphthyl and contain at least one aromatic ring. Heterocyclic aryl group include e.g. thienyl, furyl, pyridyl, indole and quinoline rings.

An aralkyl group may contain from 1 to 4 atoms in the alkyl portion and the aryl portion may be a carbocyclic or heterocyclic aryl group.

Halogen represents fluoro, chloro, bromo or iodo.

In the compound of formula (1)

X is preferably O, S or NR$^7$, wherein R$^7$ is H, C$_{1-10}$ alkyl, sulphonyl or toluene sulphonyl;

Y is preferably NR$^7$;

R$^1$ is preferably COR$^8$, COOR$^8$, CH$_2$OR$^9$, CONH$_2$, CNHMR$^{10}$R$^{11}$, CONHR$^{10}$, CONR$^{10}$R$^{11}$, COO(CH$_2$)$_n$NR$^{10}$R$^{11}$, wherein R$^8$ is H, C$_{1-10}$ alkyl, aryl containing up to 10 carbon atoms, optionally substituted by C$_{1-10}$ alkyl, C$_{1-10}$ alkoxy, halo, sulphinyl, amino (optionally substituted by one or two C$_{1-10}$ alkyl groups), haloalkyl, sulphonyl or cyano or aralkyl containing 1 to 4 carbon atoms in the alkyl portion and up to 10 carbon atoms in the aryl portion, R$^9$ is C$_{1-10}$ acyl optionally substituted by C$_{1-10}$ alkyl, C$_{1-10}$ alkoxy, halo, sulphinyl, amino (optionally substituted by one or two C$_{1-10}$ alkyl groups), haloalkyl, sulphonyl or cyano and R$^{10}$ and R$^{11}$ are independently hydrogen, C$_{1-10}$ alkyl or aryl containing up to 10 carbon atoms and n is 1 to 4 carbon atoms;

R$^2$ is preferably COOR$^8$, C$_{1-10}$ alkyl or CH$_2$CH$_2$CO$_2$R$^{12}$ wherein R$^{12}$ is C$_{1-10}$ alkyl or aryl containing up to 10 carbon atoms;

R$^3$ and R$^4$ represents independently H, hydroxy, C$_{1-10}$ alkyl, C$_{1-10}$ alkoxy, halogen, cyano, alkyl substituted by C$_{1-10}$ alkyl, C$_{1-10}$ alkoxy, halo, sulphinyl, amino (optionally substituted by one or two C$_{1-10}$ alkyl groups), haloalkyl, sulphonyl or cyano or carboxyl;

R$^5$ is preferably H or C$_{1-10}$ alkyl;

R$^6$ is preferably H, C$_{1-10}$ alkyl or aryl containing up to 10 carbon atoms and salts and physiologically functional derivatives thereof.

X preferably represents S or NA, A is preferably

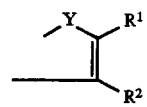

and Y preferably represents NH.

R$^1$ is preferably COOR$^8$, with R$^8$ preferably being C$_{1-10}$ alkyl or aralkyl containing 1 to 4 carbon atoms in the alkyl portion and up to 10 carbon atoms in the aryl protion.

R$^2$ is preferably H or C$_{1-10}$ alkyl.

R$^3$ is preferably H, C$_{1-10}$ alkoxy or halo.

R$^4$ is preferably H, C$_{1-10}$ alkoxy or halo.

R$^5$ is preferably C$_{1-10}$ alkyl and

R$^6$ is preferably H and salts and physiologically functional derivatives thereof.

Compounds of the general formula (I) have been tested against two specifically developed cell lines which are clones of the human fibrosarcoma cell-line, HT1080. One clone, HT1080scc2, retains the transformed phenotype of the parental line, whilst the other, HT10801c, is a morphologically flat, non-tumourigenic, revertant.

Thus, the effects of potential anti-tumour compounds can be evaluated on the basis of their ability to effect detransformation in HT1080scc2 cells.

Compounds of the present invention have been found to be particularly effective in this assay system.

In addition, compounds of the present invention have been found to be effective against MCF7 human breast cancer cells, A431 Epidermoid carcinoma cells and A285 melanoma cells.

The compounds also exhibit low toxicity against normal cells.

According to a further aspect, the present invention also provides a process for preparing compounds of general formula (I), which process comprises catalyzed ring closure of compounds of formula (IV) in the presence of a strong acid.

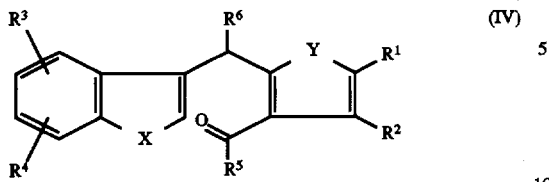

The present invention also provides for a process for preparing compounds of formula (IV) which process comprises either:
(a) Reaction of a compound of the formula (II) with a compound of the formula (III) to produce a compound of the formula (IV), wherein X,Y,$R^1$,$R^2$,$R^3$,$R^4$ and $R^5$ are as defined herein:

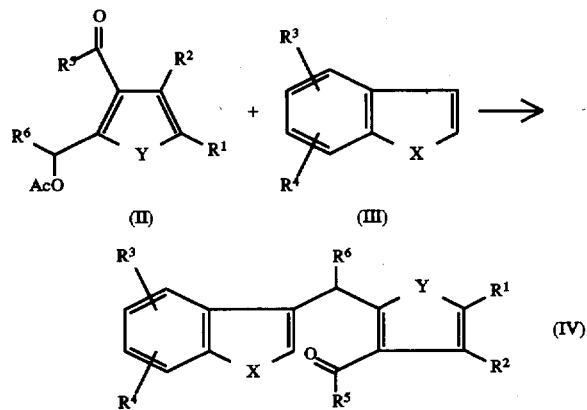

followed by catalysed ring closure.

The reaction is preferably carried out at room temperature in the presence of a strong acid, e.g. p-toluene sulphonic acid or montmorillonite K10 clay as a catalyst to produce a compound of the invention;
(b) Reaction of a compound of the formula (V) with a compound of the formula (III) to produce a compound of the formula (IV) followed as in (a) by catalyzed ring closure.

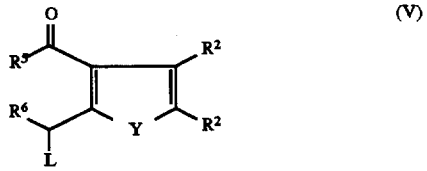

wherein L is a leaving group. Examples of suitable leaving groups include —$OCOCH_3$, OET, —$N^+Me_3$ and halo;
(c) A one step reaction procedure, reacting a compound of the formula (II) with a compound of the formula (III) in the presence of a catalyst, to produce a compound of the invention in a single step. The preferred catalyst is montmorillonite K10 clay;

Insertion of the substituent $R^1$ onto the ring system for example:
(d) Carboxylation of a polyheterocyclic compound using
  (i) a carbonyl halide or
  (ii) carbon dioxide According to known procedures (J. March, Advanced Organic Chemistry, 2nd ed, McGraw Hill, New York, 1977, p. 497–498).

(e) Alternatively one can produce compounds of the formula (I) wherein $R^2$ is CHO by methods known to those skilled in the art, for example:
  (i) The appropriate aromatic polyheterocycle can be reacted with a formylating agent, such as that generated by the reaction between $SnCl_4$ and $Cl_2CHOCH_3$ or equivalent reagents.

For example, according to the method of A. Reiche et al, Chem. Ber. 93, 88 (1960), or with other standard formylating reagents/procedures known in the art, for example, the Gatterman-Koch reaction (CO\HCl\AlCl_3\CuCl), the Gatterman reaction (HCN\HCl\ZnCl_2), and the Vilsmeir reaction ($POCl_3$\PhN-(Me)CHO or $POCl_3$\Me$_2$NHCO) (J. March, Vide Supra, p 494–497); or
  (ii) The appropriate aromatic polyheterocycle, carrying a suitable functional group, said group being converted to an aldehyde group by methods known to those skilled in the art. Suitable functional groups include $CHBr_2$, $CH_3$, $COR^{14}$, wherein $R^{14}$ is a primary or secondary $C_{1-6}$ alkyl group, COOH or a derivative thereof such as an ester, amide, acid chloride or CN; or
(f) Compounds of the formula (I) wherein $R^1$ is a $CONHR^{10}$ may also be produced by the reaction of a compound wherein $R^1$ is COOH or a suitable reactive acid derivative thereof as outlined in J. March, Vide supra. For example an acid halide can be reacted with a compound $NH_2R^{10}$ is an inert solvent.
(g) Conversion of one compound of formula (I) into another compound of formula (I).

Compounds of the invention wherein $R^1$ is $COOR^8$ and $R^8$ is, for example, aralkyl can be converted to free acids wherein $R^8$ is H by reduction in the presence of $H_2$ and a Pd catalyst, or where $R^8$ is, for example, alkyl, by hydrolysis in the presence of an appropriate base e.g. caesium carbonate.

It is thereafter possible for the skilled man to synthesize ester and amide compounds within the scope of the invention by conversion of the free acids obtained, by known procedures. (See J. March, Vide Supra, p 363–365).

Compounds of the invention produced as described herein can be converted to other compounds of the invention by electrophilic substitution at $R^5$ and/or $R^6$, to introduce, for example, $NO_2$, halogen and $COR^{13}$ wherein $R^{13}$ is as defined herein.

The above processes have been described for compounds wherein A is

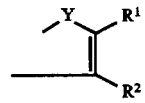

The skilled man will appreciate that these are equally applicable when A is

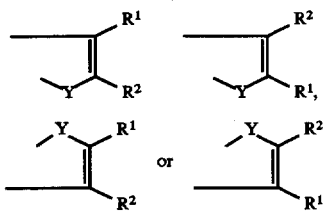

In another aspect the invention relates to novel intermediates of the formulae (II), (III), (IV) or (V).

The compounds of the present invention are useful for the treatment of tumours. They may be employed in treating various forms of cancer of mammals including carcinomas, for instance of the stomach, pancreas, breast, uterus and colon; adenocarcinomas, for instance of the lung and colon; sarcomas, for instance fibrosarcoma; leukaemias, for instance lymphocytic leukaemia and lymphomas, for instance myeloid lymphoma.

The invention thus further provides a method for the treatment of tumours in animals, include mammals, especially humans, which comprises the administration of a clinically useful amount of compound of formula (I) or a pharmaceutically acceptable salt or physiologically functional derivative in a pharmaceutically useful form, once or several times a day or in any other appropriate schedule, orally, rectally, parenterally, or applied topically.

In addition, there is provided as a further, or alternative, aspect of the invention, a compound of formula (I) or a pharmaceutically acceptable salt or physiologically functional derivative thereof for use in therapy, for example as an antitumour agent.

The amount of compound of formula (I) required to be effective against the aformentioned tumours will, of course, vary and is ultimately at the discretion of the medical or veterinary practioner. The factors to be considered include the condition being treated, the route of administration, and nature of the formulation, the mammal's body weight, surface area, age and general condition, and the particular compound to be administered. A suitable effective antitumor dose is in the range of about 0.01 to about 100 mg/kg body weight, e.g. 0.1 to about 100 mg/kg body weight, preferably 1–30 mg/kg body weight. The total daily dose may be given as a single dose, multiple doses, e.g., two to six times per day or by intravenous infusion for selected duration. For example, for a 75 kg mammal, the dose range would be about 8 to 900 mg per day, and a typical dose could be about 50 mg per day. If discrete multiple doses are indicated treatment might typically be 15 mg of a compound of formula (I) given up to 4 times per day.

Whilst it is possible for the active compound to be administered alone, it is preferable to present the active compound in a pharmaceutical formulation. Formulations of the present invention, for medical use, comprise a compound of formula (I) or a salt thereof together with one or more pharmaceutically acceptable carriers and optionally other therapeutic ingredients. The carrier(s) should be pharmaceutically acceptable in the sense of being compatible with the other ingredients of the formulation and not deleterious to the recipient thereof.

The present invention, therefore, further provides a pharmaceutical formulation comprising a compound of formula (I) or a pharmaceutically acceptable salt or physiologically functional derivative thereof together with a pharmaceutically acceptable carrier thereof.

There is also provided a method for the preparation of a pharmaceutical formulation comprising bringing into association a compound of formula (I) or a pharmaceutically acceptable salt or physiologically functional derivative thereof, and a pharmaceutically acceptable carrier thereof.

Formulations according to the present invention include those suitable for oral, topical, rectal or parenteral (including subcutaneous, intramuscular and intravenous) administration. Preferred formulations are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a solution or suspension in an aqueous or non-aqueous liquid such as a syrup, an elixir, an emulsion or a draught.

A tablet may be made by compression or moulding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Moulded tablets may be made by moulding in a suitable machine a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavourings, an agent to retard crystallisation of the sugar or an agent to increase the solubility of any other ingredients, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitable comprise a solution of a pharmaceutically and pharmacologically acceptable acid addition salt of a compound of the formula (I) that is isotonic with the blood of the recipient.

Useful formulations also comprise concentrated solutions or solids containing the compound of formula (I) which upon dilution with an appropriate solvent give a solution for parenteral administration as above.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

In a further aspect of the present invention provides the use of a compound of formula (I) or a pharmaceutically acceptable salt or physiologically functional derivative thereof for the manufacture of a medicament for the treatment of tumours.

The invention will now be illustrated by the following non-limiting Examples:

All temperatures are in degrees Celcius (°C.)

IR spectra were recorded on a Perkin-Elmer 257 grating spectrophotometer or a Bruker FS66 spectrophotometer.

U.V. spectra were measured in ethanol on a Unicam SP800 spectrophotometer.

1H NMR spectra were obtained on a Bruker WM 360-NMR spectrophotometer at 360 MHz, or on a Bruker AC200 spectrophotometer at 200 MHz. J values are given in Hz.

Mass spectra were obtained on Varian CH5D(EI), Kratos Concept (EI) or Kratos Ms50(FAB) instruments.

EXAMPLE 1

Preparation of Intermediates

Preparation of Pyrroles

Ethyl 4-acetyl-3,5-dimethylpyrrole-2-carboxylate, benzyl 4-acetyl-3,5-dimethylpyrrole-2-carboxylate and ethyl 4-acetyl-3-ethyl-5-methylpyrrole-2-carboxylate) were prepared according to the method of A. W. Johnson et al, *J. Chem. Soc.*, 4254 (1958).

N-Methylation of Pyrroles—General Procedure

A mixture of the pyrrole (20 mmol) methyl iodide (50 mmol) and potassium carbonate (50 mmol) was heated to reflux in methyl ethyl ketone (50 ml) for 8 h. If TLF (toluene/ethyl acetate 3:1) indicated incomplete reaction, further aliquots of methyl iodide (50 mmol) and potassium carbonate (50 mmol) were added and the mixture heated to reflux for a further 6 h. After evaporation in vacuo to dryness, the residue was taken up in warm water and extracted with ethyl acetate (3×50 ml). The combined extracts were dried over magnesium sulphate and evaporated in vacuo to leave a yellow oil or solid which was crystallised from aqueous ethanol.

Ethyl 4-acetyl-1,3,5-trimethylpyrrole-2-carboxylate

Obtained from ethyl 4-acetyl-3,5-dimethylpyrrole-2-carboxylate as white crystals (2 g; 4%) m.p. 61°–62° C. (Found: C, 64.17; H, 7.82; N 6.16 $C_{12}H_{17}NO_3$ requires C, 64.55; H, 7.68; N, 6.27%) $\delta_H([^2H_6]$-DMSO) 4.25 (2H, q, $CH_2CH_3$), 3.70 (3H, s, 1-$CH_3$), 2.43 and 2.42 (2 x 3H, 2 x s, 3-$CH_3$ and $COOH_3$), 2.38 (3H, s, 5-$CH_3$) and 1.29 (3H, t, $CH_2CH_3$); m/z (%) 224(MH$^+$, 100), 208(40), 194(20), 178 (40) and 133(20)(FAB); $\nu_{max}$ (KBr Disc)/CM$^{-1}$ 2984, 1691 and 1651.

Benzyl 4-acetyl-1,3,5-trimethylpyrrole-2-carboxylate

Obtained from benzyl 4-acetyl-3,5-eimethyl-2-carboxylate as white crystals m.p. 78°–79° C. (Found: C, 71.30; H, 6.74; N, 4.79; $C_{17}H_{19}NO_3$ requires C, 71.56; H, 6.71; N, 4.91%); $\delta_H$ ([$^2H_6$]-DMSO) 7.52-7.27 (5 H, m, ArH), 5.30 (2 H, s, $CH_2Ph$), 3.73 (3 H, s, 1-$CH_3$), 2.42 (6 H, s, 3-$CH_3$ and $COCH_3$) and 2.38 (3 H, s, 5-$CH_3$); m/z (%) 285(76, M$^+$), 270(87), 194(53), 178(23), 151(36), 136(26) and 91(100); $\nu_{max}$ (KBr Disc)/cm$^{-1}$ 2974, 1693 and 1641.

Preparation of the 5-Acetoxymethyl-4-acetylpyrroles—General procedure

To a cooled (0° C.) and stirred suspension of the 4-acetyl-5-methylpyrrole (0.02 mol) in dry diethyl ether (20 cm$^3$) was added, dropwise over 15 min, freshly distilled sulfuryl chloride (2.2 cm$^3$, 1.25 equiv.). The reaction mixture was stirred further and the chloromethyl derivative crystallised out slowly, filtration gave the 5-chloromethyl derivative as colourless crystals. The purity of the chloromethylpyrrole was checked by $^1$H NMR spectroscopy (90 MH$_z$) and it was used directly without recrystallisation.

The above chloromethylpyrrole (0.01 mol) was added to a solution of sodium acetate (3 g) in acetic acid (50 cm$^3$), the mixture stirred for 2 h and poured into ice-water (200 cm$^3$). The resulting solid was washed well with water until acid-free before drying.

Ethyl 5-acetoxymethyl-4-acetyl-3-methylpyrrole-2-carboxylate crystallised from benzene as colourless needles (1.87 g, 70%) m.p. 135.5°–138° C. (Found: C, 58.6; H, 6.45; N, 5.15.$C_{13}H_{17}NO_5$ requires C, 58.4; H, 6.41; N, 5.24%); $\delta_H(CDCl_3)$ 9.57 (1 H, br s, NH), 5.40 (2 H, s, $CH_2OAc$), 4.35 (2 H, q, $OCH_2CH_3$), 2.6 (3 H, s, 3-$CH_3$) 2.5 (3 H, s, $COCH_3$), 2.17 (3 H, s, $OCOCH_3$) and 1.4 (3 H, t, $OCH_2CH_3$); m/z (%) 267(83,M$^+$), 224(46), 207(27), 178 (100) and 162(42).

Benzyl 5-acetoxymethyl-4-acetyl-3-methylpyrrole-2-carboxylate crystallised from methanol as colourless needles (2.34 g, 71%) m.p. 138°–141° C. (Found: C, 65.8; H, 5.95; N, 4.3 $C_{18}H_{19}NO_5$ requires C, 65.64; H, 5.81; N, 4.25%); $\delta_H(CDCl_3)$ 9.44 (1 H, br s NH), 7.49-7.32 (5 H,m,ArH), 5.40 (2 H,s,$CH_2OAc$), 5.35 (2 H,s,$CH_2Ph$), 2.62 (3 H,s,3-$CH_3$), 2.49 (3 H,s,$CH_3CO$) and 2.14 (3 H,s,$OCOCH_3$); m/z (%) 329 (9,M$^+$), 286 (13), 269(4), 178(19) and 91(100).

In the case of benzyl 5-acetoxymethyl-4-acetyl-3-(2-methoxycarbonylethyl)-pyrrole-2-carboxylate, there was no precipitation when the solution was poured into ice-water. Extraction with chloroform (3×100 cm$^3$), drying and removal of solvent under reduced pressure gave an oil which was crystallised from benzene-light petroleum to yield colourless needles (2.69 g, 67%) m.p. 97°–100° C. (Found C, 62.9; H 5.9; N 3.45. $C_{21}H_{23}NO_7$ requires C,62.8; H, 5.78; N, 3.49%); $\delta_H(CDCl_3)$ 9.15 (1 H, br s,NH), 7.50-7.30 (5 H, m, ArH), 5.35 (4 H, s, $CH_2Ph$ and $CH_2OAc$), 3.63 (3 H, s, $OCH_3$), 3.37 (2 H, t, $CH_2CH_2CO$), 2.58 (2 H, t, $CH_2CO$), 2.51 (3 H,s,$COCH_3$) and 2.15 (3 H,s,$OCOCH_3$); m/z(%) 401(4,M$^+$), 341(8), 268(6),250(60) and 91(100).

Ethyl 5-acetoxymethyl-4-acetyl-1,3-dimethylpyrrole-2-carboxylate

Crystallised from ethyl acetate/cyclohexane (61%) m.p. 100°–101° C. (Found: C, 59.38; H, 6.73; N, 4.95. $C_{14}H_{19}NO_5$ requires C, 59.78; H, 6.81; N, 4.98%); $\delta_H([^2H_6]$-DMSO 5.30 (2 H, s, $CH_2OAc$), 4.29 (2 H, q, $CH_2CH_3$), 3.77 (3 H, s, N-$CH_3$), 2.43 and 2.42 (2×3 H, 2×s, 3-$CH_3$ and $CH_3CO$), 2.02 (3 H, s, $OCOCH_3$) and 1.31 (3 H, t, $CH_2CH_3$); m/z (%) 281 (34,M$^+$), 238(100), 222(48) and 192(52); $\nu_{max}$ (KBr Disc)/cm$^{-1}$ 1712 and 1697.

Benzyl 5-acetoxymethyl-4-acetyl-1,3-dimethylpyrrole-2-carboxylate

Crystallised from ethyl acetate/cyclohexane. $\delta_H$ ($^2[H]_6$-DMSO) 7.51-7.32 (5 H, m, ArH), 5.34 and 5.32 (2×2 H, 2×s, $CH_2Ph$ and $CH_2OAc$), 3.78 (3 H, s, N-$CH_3$), 2.46 and 2.45 (2×3 H, 2×s, 3-$CH_3$ and $CH_3CO$) and 2.04 (3 H, s, $OCOCH_3$); m/z (%) 343(5, M$^+$), 284(100) and 91(95).

Ethyl 5-acetoxymethyl-4-acetyl-3-ethylpyrrole-2-carboxylate

Crystallised from ether/petrol as fawn needles (61%) with m.p. 97°–98° C. (Found: C, 59.44; H, 6.78; N, 4.80. $C_{14}H_{19}NO_5$ requires: C, 59.76; H, 6.81; N, 4.98%); $\delta$H (CDCl$_3$) 9.40 (1 H, br s, 1-NH), 5.38 (2 H, s, $CH_2OAc$), 4.38 (2 H, q, J 7, $CO_2CH_2$), 3.10 (2 H, q, J 7.5, 3-c$H_2$), 2.54 (3 H, s, $COCH_3$), 2.18 (3 H, s, $OCOCH_3$), 1.40 (3 H, t, J 7.5, $CO_2CH_2CH_3$), 1.23 (3 H, t, J 7.5, 3-$CH_2CH_3$); m/z (%) 281 (42, M$^+$), 238(61), 221(89), 206(58), 192(92), 175(95), 160(81), 147(59), 43(100); $\nu_{max}$ (KBr disc)/cm$^{-1}$ 3277, 1738, 1674, 1657.

Synthesis of the 3-(Pyrrolylmethyl)indole, 2-(Pyrrolylmethyl)benzofuran and 3-(Pyrrolylmethyl) benzothiophene—General procedure A solution of the 5-acetoxymethyl-4-acetylpyrrole (1.0 mmol) and indole (1.0 mmol) in 1,2-dichloroethane (10 cm$^3$) was heated at gentle reflux and stirred with Montmorillonite clay (1 g) for 1.5–2 h. After filtration from caly and washing well with 1,2-dichloroethane, evaporation of the combined filtrates under reduced pressure gave an oil. This oil was submitted to flash chromatography on silica, eluting with ethyl acetate in light petroleum to give 3-(3'-acetyl-5'-ethoxycarbonyl-4'-methylpyrrol-2'-ylmethyl)indole. It gave colourless crystals from ethyl acetate-light petroleum (0.1465 g, 45%). m.p. 180°–182° C. (Found: C,70.5; H, 6.25; N, 8.65. $C_{19}H_{20}N_2O_3$ requires C, 70.4; H, 6.21; N, 8.64%); $\delta_H$(CDCl$_3$) 8.78 (1 H, s, pyr-NH), 8.27 (1 H, s, ind-NH), 7.45 (1 H, d, J7,4-H) 7.42 (1 H, d, J7, 7-H) 7.25 (1 H, t, J7, 6-H), 7.14 (1 H, t, J7, 5-H), 7.10 (1 H, s, 2-H), 4.45 (2 H, s, 3-CH$_2$), 4.22 (2 H, q, OCH$_2$CH$_3$), 2.63 (3 H, s, 4'-CH$_3$) 2.53 (3 H, s, CH$_3$CO) and 1.25 (3 H, t, OCH$_2$CH$_3$); m/z (%) 324(100,M$^+$) 309(48), 277(25), 263(54), 250 (38),235(30),207(48), 139(24),130(30),117(67) and 90(16); $v_{max}$(CHCl$_3$)/cm$^{-1}$ 3490, 3430, 1680 and 1650.

Benzofuran (1.0 mmol) when used instead of indole, after chromatography, gave 2-(3'-acetyl-5'-ethoxycarbonyl-4'-methylpyrrol-2'-ylmethyl)benzofuran (0.106 g, 32.6%), m.p. 124°–127° C. (Found: C, 70.1; H, 6.1; N, 4.15 $C_{19}H_{19}NO_4$ requires C, 70.14; H, 5.89; N, 4.31%); $\delta_H$(CDCl$_3$) 9.25 (1 H, s, NH), 7.50(1 H, d, J7.3, 4-H) 7.44 (1 H, d, J7.3, 7-H) 7.28-7.18 (2 H, m, 6-H and 5-H), 6.57 (1 H, s, 3-H), 4.50 (2 H, s, 2-CH$_2$), 4.31 (2 H, q, OCH$_2$CH$_3$) 2.62 (3 H, s, 4'-CH$_3$) 2.50 (3 H, s, CH$_3$CO) and 1.35 (3 H, t, OCH$_2$CH$_3$); saturation of the singlet 3-H at $\delta$ 6.51 enhanced the signals due to 4 H at $\delta$7.50 (2.7%) and 2-CH$_2$ at $\delta$ 4.50 (0.8%); m/z (%) 325(100,M$^+$), 310(4),279(29), 264(17), 215(59), 236(27), 208(19), 193(9), 131(7) and 118(7); and the 2,3-bis (3'-acetyl-5'-ethoxycarbonyl-4'-methylpyrrol-2'-ylmethyl)benzofuran (0.0238 g, 8.94%) m.p. 255°–257° C.; $\delta_H$ (CDCl$_3$) 10.09 (1 H, s, NH) 9.95 (1 H, s, NH), 7.32 (1 H, d, J7.7, 4-H), 7.27 (1 H, d, J7.7, 7-H), 7.17 (1 H, t, J7.7, 6-H), 7.08 (1 H, t, J7.7, 5-H) 4.45 (2 H, s, 2-CH$_2$), 4.40 (2 H, s, 3-CH$_2$), 4.36 (2 H, q, OCH$_2$CH$_3$), 4.27 (2 H,q,OCH$_2$CH$_3$), 2.64(3 H,s,4'-CH$_3$), 2.63(3 H,s,4'-CH$_3$), 2.58 (3 H, s, CH$_3$CO), 2.54 (3 H, s, CH$_3$CO), 1.39 (3 H, t, OCH$_2$CH$_3$) and 1.31 (3 H, t, OCH$_2$CH$_3$); m/z (%) 532(11,M$^+$), 490(24), 444(9), 397(6), 324(100), 282 (18), 278(27), 236(20), 209(28) and 162(28) (Found: M$^+$,532.2210. $C_{30}H_{32}N_2O_7$ requires M, 532.2209).

When benzothiophene (1.0 mmol) was used in the same way as indole, chromatography using ethyl acetate in dichloromethane as eluent gave colourless crystals of 3-(3'-acetyl-5'-ethoxycarbonyl-4'-methylpyrrol-2'-ylmethyl)benzothiophene (0.0963 g, 28.2%) m.p.125°–128° C. (Found: C, 6675; h, 5.8; N,4.1 $C_{19}H_{19}NO_3S$ requires C, 66.84; H, 5.61; N, 4.10%); $\delta_H$(CDCl$_3$) 8.72 (1 H, br, s, NH), 7.88 (1 H, m, 4-H), 7.63 (1 H, m, 7-H), 7.37 (2 H, m, 6-H and 5-H), 7.20 (1 H, s, 2-H), 4.54 (2 H, s, 3-CH$_2$), 4.23 (2 H, q, OCH$_2$CH$_3$), 2.62 (3 H, s, 4'-CH$_3$), 2.53 (3 H, s, CH$_3$CO) and 1.28 (3 H, t, OCH$_2$CH$_3$); saturation of the 3-CH$_2$ protons at $\delta$ 4.54 enhanced the signals due to NH at $\delta$ 8.72 (3.3%), 4-H at $\delta$ 7.88 (7.7%), 2-H at $\delta$ 7.20(6%) and CH$_3$CO at $\delta$2.53 (1.3%); m/z (%) 341(100,M$^+$), 326(9), 298(6), 295(20), 230(39), 267(46), 252(32), 224(27), 194 (26) and 148(22); and the 2,3-bis (3'-acetyl-5'-ethoxycarbonyl-4'-methylpyrrol-2'-ylmethyl) benzothiophene as a pale yellow solid (0.0264 g, 9.6%), m.p. 206°–209° C. (Found: c, 65.6; H, 5.8; N 5.1 $C_{30}H_{32}N_2O_6S$ requires C, 65.67; H, 5.88; N, 5.11%), $\delta_H$(CDCl$_3$) 9.77 (1 H, br, s, NH), 9.43 (1 H, br, s, NH), 7.70 (1 H, m, 4-H), 7.49(1 H, m, 7-H), 7.26 (2 H, m, 6-H and 5-H), 4.55 2 H, s, CH$_2$), 4.53(2 H, s, CH$_2$), 4.32 (2 H, q, OCH$_2$CH$_3$), 4.24 (2 H, q, OCH$_2$CH$_3$), 2.61 (3 H, s, 4'-CH$_3$), 2.60 (3 H, s, 4'-CH$_3$), 2.57 (3 H, s, CH$_3$CO) 2.49 (3 H, s, CH$_3$CO), 1.35 (3 H,t,OCH$_2$CH$_3$) and 1.28 (3 H,t,OCH$_2$CH$_3$); m/z(%) 548(5,M$^+$), 530(11), 340(100), 294(27) and 162(10).

EXAMPLE 2

Synthesis of 3-(Pyrrolylmethyl)benzothiophenes and 3-(Pyrrolylmethyl)indoles a) 3-(3'-Acetyl-5'-benzyloxycarbonyl-4'-methylpyrrol-2'-ylmethyl)benzothiophene A solution of the 5-acetoxymethyl-4-acetylpyrrole (0.33 g; 1.0 mmol) and benzothiophene (0.14 g; 1.05 mmol) in 1,2-dichloroethane (10 cm$^3$) was heated at reflux and stirred with Montmorillonite K10 clay (1 g) for 2.5 h. After cooling and filtration from the clay, which was washed well with 1,2-dichlorethane, the combined filtrates were evaporated under reduced pressure to leave a yellow oil. Flash chromatography on silica, eluting with diethyl ether/light petroleum (1:2) gave the title compound as a colourless solid.

$\delta_H$(CDCl$_3$) 8.72 (1 H, s, NH), 7.92-7.84 (1 H, m, 4-H), 7.69-7.58 (1 H, m, 7-H), 7.43-7.16 (8 H, m, 2-H, 5-H, 6-H, ArH), 5.23 (2 H, s, CH$_2$Ph), 4.50 (2 H, s, 3-CH$_2$), 2.61 (3 H, s, 4'-CH$_3$) and 2.50 (3 H, s, CH$_3$CO); m/z (%) 403 (M+, 100), $v_{max}$ (KBr Disc)/cm$^{-1}$ 3290, 1690 and 1659.

b) 3-(3'-Acetyl-5'-ethoxycarbonyl-4'-methylpyrrol-2'-ylmethyl)-5-cyanoindole

A solution of the 5-acetoxymethyl-4-acetylpyrrole (0.7 g, 2.6 mmol) and 5-cyanoindole (0.41 g, 2.9 mmol) in 1,2-dichloroethane (50 cm$^3$) was heated at reflux and stirred with Montmorillonite K10 clay (2.1 g) for 6 h. After cooling and filtration from the clay, which was washed well with 1,2-dichloroethane, the combined filtrates were evaporated under reduced pressure to leave an orange solid. Crystallisation from dichloromethane/ethyl acetate yielded a small amount of analytically pure title compound as cream crystals. The evaporated mother liquors were submitted to flash chromatography on silica, eluting with dichloromethane/ethyl acetate (9:1) to give further product (0.65 g, 71%). m.p. 213°–214° C. (Found: C, 68.60; H, 5.46; N, 11.99. $C_{20}H_{19}N_3O_3$ requires C, 68.75; H, 5.48; N, 12.03%) $\delta_H$( [$^2$H$_6$]-DMSO) 12.05 (1 H, s, 1'-NH), 11.38 (1 H, s, 1-NH), 8.20 (1 H, m, 4-H), 7.50 (1 H, dd, J0.7 and 8.5, 7-H), 7.39 (1 H, dd, J1.7 and 8.5, 6-H), 7.18 (1 H, s, 2-H), 4.32 (2 H, s, 3-CH$_2$ 4.27 (2 H, q, CH$_2$CH$_3$), 2.33 (3 H, s, 4'-CH$_3$), 2.51 (3 H, s, CH$_3$CO) and 1.30 (3 H, t, CH$_2$CH$_3$); m/z (%) 350(M$^+$, 70), 302(16), 279(18), 237(35), 208(100) and 181 (20); $v_{max}$(KBr Disc)/cm$^{-1}$ 3309, 2218 and 1665.

c) 3-(3'-Acetyl-5'-ethoxycarbonyl-4'-methylpyrrol-2'-ylmethyl)indole-5-carboxylic acid A solution of the 5-acetoxymethyl-4-acetylpyrrole (0.74 g, 2.8 mmol) and indole-5-carboxylic acid (0.5 g, 3 mmol) in toluene (50 cm$^3$) was stirred at room temperature with Montmorillonite K10 clay (1 g) for 10 days. After coolinbg and filtration from the clay, which was washed well with toluene, the combined filtrates were evaporated under reduced pressure to leave an orange solid. Crystallisation from ethyl acetate/cyclohexane yielded the title compound as a grey powder (0.15 g, 15%). m.p. 227°–228° C. (Found: C, 64.96; H, 5.58; N, 7.34. $C_{20}H_{20}N_2O_5$ requires C, 65.21; H, 5.47; N, 7.60%); $\delta_H$([$^2$H$_6$]-DMSO) 12.35 (1 H, br, CO$_2$H) 12.04 (1 H, s, 1'-NH), 11.17 (1 H, s, 1-NH), 8.31 (1 H, d, J1.6, 4-H), 7.70 (1 H, dd, J1.6 and 8.7, 6-H), 6.98 (1 H, s, 2-H), 4.36 (2 H, s, 3-CH$_2$), 4.26 (2 H, q, CH$_2$CH$_3$), 2.51 and 2.31 (2×3 H, 2×s, 4'-CH$_3$ and CH$_3$CO) and 1.29 (3 H, t,CH$_2$CH$_3$); m/z (%) 369(22(M+1)$^+$), 351(37), 323(18), 305 (19), 232(19), 208(60) and 181(20), 162(100); $v_{max}$(KBr disc)/cm$^{-1}$ 3359 and 1676.

d) 3-(3'-Acetyl-5'-ethoxycarbonyl-4'-methylpyrrol-2'-ylmethyl)-5-bromoindole

A solution of the 5-acetoxymethyl-4-acetylpyrrole (1.3 g, 4.9 mmol) and 5-bromoindole (1.09 g, 5.6 mmol) in 1,2-dichloroethane (100 cm$^3$) was heated at reflux and stirred with Montmorillonite K10 clay (3 g) for 5 h. After cooling and filtration from the clay, which was washed well with 1,2-dichloroethane, the combined filtrates were evaporated under reduced pressure to leave a yellow solid. Crystallisation from dichloromethane/light petroleum/acetone yielded the title compound as cream crystals (0.33 g, 17%). m.p. 181°–183° C. (Found: C, 56.24; H, 4.70; N, 6.86. $C_{19}H_{19}BrN_2O_3$ requires C, 56.59; H, 4.75; N, 6.95%); $\delta_H$([$^2H_6$]-DMSO) 12.00 (1 H, s, 1'-NH), 11.00 (1 H, s, 1-NH), 7.82 (1 H, d, J1.9, 4-H), 7.31 (1 H, d, J8.6, 7-H), 7.16 (1 H, dd, J1.9 and 8.6, 6-H), 7.02 (1 H, s, 2 H), 4.30 (2 H, s, 3-CH$_2$), 4.28 (2 H, q, CUHU$_2$CH$_3$), 2.51 and 2.33 (2×3 H, 2×s, 4'-CH$_3$ and CH$_3$CO) 1.31 (3 H, t, CH$_2$CH$_3$) m/z (%) 404 and 402(100 M$^+$), 389 and 387(24), 357(24), 330 and 328(32), 206(36) and 178(26); $v_{max}$(KBr disc)/cm$^{-1}$ 3373 and 1672.

EXAMPLE 3 a) Ethyl 3,4-dimethylpyrrolo[3,2,-b]carbazole-2-carboxylate

A solution of the 3-(pyrrolylmethyl)indole (0.108 g 0.33 mmol) was heated at gentle reflux in 1,2-dichloroethane (10 cm$^3$) and stirred with Montmorillonite K10 clay (1 g) for 2 h. TLC then showed a single compound had been formed and that reaction was complete. After filtration from clay and washing well with 1,2-dichloroethane, evaporation of the combined filtrates under reduced pressure gave a yellow solid which crystallised from ethyl acetate to give the pyrrolo[3,2-b]-carbazole as yellow crystals (0.076 g; 75%), m.p. 209.5°–211° C. (Found: C, 74.6; H, 6.14; N, 9.03. $C_{19}H_{18}N_2O_2$ requires C.74.5; H, 5.92; N, 9.14%); $\delta_H$[$^2H_6$]-DMSO 11.22 (1 H, s, 1-NH), 10.70 (1 H, s, 5-NH), 8.06 (1 H, d, J7, 9-H), 7.85 (1 H, s, 10-H), 7.40 (1 H, d, J7, 6-H), 7.35 (1 H, t, 7-H), 7.08 (1 H, t, J7, 8-H), 4.35 (2 H, q, OCH$_2$CH$_3$) 2.91 and 2.90 (2×3 H, 2×S, 3-CH$_3$ and 4-CH$_3$ and 1.35 (3 H, t, OCH$_2$CH$_3$). Saturation of the 10-H at δ 7.85 enhanced the singlets due to 1-NH at δ 11.22 (3%) and 9-H at δ 8.06 (4%); m/z (%) 306(56,M$^+$), 260(100), 323(39), 205(15), 140(18) and 130(26); $v_{max}$(CHCl$_3$)/cm$^{-1}$ 3480 and 1700; $\lambda_{max}$(EtOH)/nm 226, 268, 310 sh, 327 sh, 340, 390 and 410 sh.

b) Ethyl 3,4-dimethyl-1H-benzofuro[3,2,-f]indole-2-carboxylate

Toluene-p-sulfonic acid (50 mg) was added to a solution of the 2-(pyrrolylmethyl)benzofuran (0.100 g 0.31 mmol) in toluene (10 cm$^3$), and the reaction mixture was heated under reflux for 3 h. On cooling, the product crystallised out, and after filtration and washing with ethanol gave the title compound as pale yellow crystals (0.84 g, 88.8%), m.p. 262°–265° C. (found: C, 74.25; H, 5.55; N, 4.6 $C_{19}H_{17}NO_3$ requires C. 74.25; H, 5.56; N, 4.56%); $\delta_H$([$^2H_6$]-DMSO) 11.52 (1 H, s, 1-NH). 8.18 (1 H, d, J7.5, 5-H), 7.62 (1 H, d, J7.5, 8-H), 7.46 (1 H, t, J7.5, 7-H), 7.38 (1 H, t, J7.5, 6-H) 7.38 (1 H, s, 10-H), 4.37 (2 H, q, OCH$_2$CH$_3$), 3.14 (3 H, s, 4-CH$_3$), 2.91 (3 H, s, 3-CH$_3$) and 1.39 (3 H, t, OCH$_2$CH$_3$); saturation of the 4-CH$_3$ at δ 3.14 enhanced the signals due to 5-H at δ 8.18 (4.5%) and 3-CH$_3$ at δ 2.91 (2.6%); m/z (%) 307 (53,M$^+$), 261(100), 233(31) and 205 (9); $v_{max}$(Nujol)/cm$^{-1}$ 3350 and 1686; $\lambda_{max}$(EtOH)/nm 240, 269,293,330 and 344.

c) Ethyl 3,4-dimethyl-1H-[1]benzothieno[2,3-f]indole-2-carboxylate

Toluene-p-sulfonic acid (45 mg) was added to the solution of the 3-(pyrrolylmethyl)benzothiophene (0.100 g, 0.29 mmol) in toluene (10 cm$^3$) and the reaction mixture was heated under reflux for 3 h. Evaporation of the solvent and washing the resulting solid with ethanol gave the title compound as a pale yellow solid (0.0758 g, 80%), m.p. 191°–193° C. (Found: C, 70.3; H 5.5; N, 4.2. $C_{19}H_{17}NO_2S$ requires C, 70.6; H, 5.30; N, 4.33%); $\delta_H$([$^2H_6$]-DMSO) 11.64 (1 H, s, NH), 8.25(1 H, m, 9-H), 8.12 (1 H, s, 10-H) 7.95 (1 H, m, 6-H), 7.48 (2 H, m, 7-H and 8-H), 4.38 (2 H, q, OCH$_2$CH$_3$), 2.87 and 2.85 (2×3 H, 2×S, 3-CH$_3$) and 1.37 (3 H, t, OCH$_2$CH$_3$); m/z (%) 323(53,M$^+$), 277(100), 249 (33), 221(15), 139(7) and 111(11); $v_{max}$(Nujol)/cm$^{-1}$ 3350 and 1686; $\lambda_{max}$(EtOH)/nm 240,269,293,330 and 344.

d) Benzyl 3,4-dimethyl-1H-[1]benzothieno[2,3-f]indole-2-carboxylate

Toluene-p-sulphonic acid (40 mg) was added to the solution of the 3-(pyrrolylmethyl)benzothiophene )0.100 g, 0.25 mmol) in toluene (12 cm$^3$) and the reaction heated under reflux for 6 h. Evaporation of the solvent and washing the resultant solid with ethanol gave the title compound as a pale yellow solid (0.02 g, 20%) m.p. 203°–204° C. (Found: C, 74.7; H, 4.9; N, 3.6; $C_{24}H_{19}NO_2S$ requires C, 74.8; H, 5.0; N, 3.6%); $\delta_H$ ([$^2H_6$]-DMSO) 11.64 (1 H, s, NH) 8.27-8.15 (1 H, m, 9-H), 8.10 (1 H, s, 10-H), 7.90-7.89 (1 H, m, 6-H). 7.60-7.30 (7 H, m, 7-H, 8-H, ArH), 5.40 (2 H, s, CH$_2$) and 2.87 (6 H, s, 2×CH$_3$); m/z (%) 385(100, M$^+$), 277(89), 248(25), 221(15) and 91(28); $v_{max}$(KBr Disc/cm$^{-1}$ 3331 and 1672.

e) Ethyl 8-cyano-3,4-dimethylpyrrolo[3,2-b]carbazole-2-carboxylate

A mixture of the 3-(pyrrolylmethyl)indole (0.6 g, 1.7 mmol) and Montmorillonite K10 clay (2 g) in toluene was stirred and heated at reflux for 24 h. After cooling and filtration from the clay, which was washed well with toluene, the combined filtrates were evaporated under reduced pressure to leave a brown solid which was submitted to flash chromatography on silica, eluting with cyclohexane/ethyl acetate (3:1) to give a yellow solid. Crystallisation from cyclohexane/ethyl acetate yielded the title compound as a yellow powder (0.030 g, 5%). m.p.>240° C. (Found: C, 71.54; H, 5.18; N, 12.78, $C_{20}H_{17}N_3O_2.0.2H_2O$ requires C, 71.71; H, 5.24; N, 12.54%) $\delta_H$([$^2H_6$]-DMSO) 11.39 (1 H, s, 1-NH), 11.29 (1 H, s, 5-NH), 8.65 (1 H, d, J1.7, 9-H), 8.01 (1 H, s, 10-H), 7.71 (1 H, dd, J1.7 and 8.6, 7-H), 7.50 (1 H, d, J8.6, 6-H), 4.36 (2 H, q, CH$_2$CH$_3$), 2.91 and 2.89 (2×3 H, 2×s, 4-CH$_3$ and 3-CH$_3$) and 1.38 (3 H, t, CH$_2$CH$_3$); m/z (%) 331 (52,M$^+$) 285(100), 256(32), 229(12), 167(14) and 149 (40); $v_{max}$(KBr Disc)/cm$^{-1}$ 3414, 3550, 2212 and 1664.

f) 3,4-Dimethyl-2-ethoxycarbonylpyrrolo[3,2-b]carbazole-8-carboxylic acid

A mixture of the 3-(pyrrolylmethyl)indole (0.1 g, 0.3 mmol) and Montmorillonite K10 clay (0.34 g) in toluene (15 cm$^3$) was stirred and heated at reflux for 6 h. After cooling and filtration from the clay, which was washed well with toluene, the combined filtrates were evaporated under reduced pressure to leave an orange solid. crystallisation from methanol/dichloromethane yielded the title compound as a yellow powder (0.027 g, 28%). m.p >260° C. (Found: C, 68.12; H, 5.19; N, 7.91 $C_{20}H_{18}N_2O_4.0.05H_2O$ requires C, 68.39; H, 5.19; N, 7.98%); $\delta_H$($^2$[H]$_6$-DMSO) 12.42 (1 H, br, COOH), 11.30 (1 H, s, 1-NH), 11.09 (1 H s, 5-NH), 8.68 (1 H, s, 10-H), 8.07-7.93 (2 H, m, 7-H and 9-H), 7.45 (1 H, d, J9, 6-H), 4.38 (2 H, q, CH$_2$CH$_3$), 2.94 and 2.90 (2×3 H, 2×s, 4-CH$_3$ and 3-CH$_3$) and 1.39 (3 H, t, CH$_2$CH$_3$); m/z (%) 350(100, M$^+$), 304(100), 278(40), 232(35) and 181(38); $v_{max}$ (KBr Disc)/cm$^{-1}$ 3459, 1697 and 1674.

g) Ethyl 8-bromo-3,4-dimethylpyrrolo[3,2-b]bicarbazole-2-carboxylate

A mixture of the 3-pyrrolylmethyl)indole (0.3 g, 0.74 mmol) and Montmorillonite K10 clay (1 g) in toluene was stirred and heated at reflux for 6 h. After cooling and filtration from the clay, which was washed well with toluene, the combined filtrates were evaporated under reduced pressure to leave a brown solid which was submitted to flash chromatography on silica, eluting with dichloromethane/light petroleum (7:3) to give a yellow solid. Crystallisation from cyclohexane/ethyl acetate yielded the title compound as a yellow powder (0.070 g, 24%). m.p. 204°–205° C. (decomp.) (Found: C,59.17; H, 4.43; N, 7.30. $C_{19}H_{17}BrN_2O_2$ requires C, 59.23; H, 4.45; N, 7.27%); $\delta_H([^2H_6]$-DMSO) 11.26 (1 H, s, 1-NH), 10.79 (1 H, s, 5-NH), 8.30 (1 H, d, J2.2, 9-H), 7.92 (1 H, s, 10-H), 7.47 (1 H, dd, J2.22 and 8.8,7 -H), 7.35 (1 H, d, J8.8, 6-H), 4.36 (2 H, q, C$\underline{H}_2$CH$_3$), 2.89 and 2.88 (2×s, 4-CH$_3$ and 3-CH$_3$) and 1.38 (3 H, t, CH$_3$C$\underline{H}_3$); m/z (%) 386 and 384(100, M$^+$), 340 and 338(70), 232(60) and 181(50); $v_{max}$(KBr Disc)/cm$^{-1}$ 3350, 1705 and 1663.

EXAMPLE 4

One-pot Synthesis of the Pyrrolocarbazoles— General procedure

A solution of indole (1.0 mmol) and the 5-acetoxymethyl-4-acetylpyrrole (1.0 mmol) in 1,2-dichloroethane (10 cm$^3$) was heated under gentle reflux and stirred with Montomorillonite K10 clay (1 g) for 3–4 h. The colour of clay turned light brown and the reaction was followed to completion by TLC. After filtration from clay and washing well with 1,2-dichloroethane, evaporation of the combined filtrates gave the pyrrolo[3,2-b]carbazoles which were obtained as yellow crystals after crystallisation fromm dichloromethane or ethyl acetate.

a) Ethyl 3,4-dimethylpyrrolo[3,2,-b]carbazole-2-carboxylate (0.199 g, 65%) was obtained from the reaction of indole and the 5-acetoxymethyl-4-acetylpyrrole. It was identical in all respects to the pyrrolo[3,2-b]carbazole from example 1.

b) Benzyl 3,4-dimethylpyrrolo[3,2-b]carbazole-2-carboxylate (0.179 g, 48.8%) was obtained from the reaction between indole and the 5-acetoxymethyl-4-acetylpyrrole, it had m.p. 229°–232° C. (Found: C, 78.2; H, 5.65; N, 7.8. $C_{24}H_{20}N_2O_2$ requires C, 78.23; H, 5.47; N,7.60%); $\delta_H([^2H_6]$-DMSO-d$_6$) 11.29 (1 H, s, 1-NH), 10.65 (1 H, s, 5-NH),8.08 (1 H, d, J8, 9-H), 7.89 (1 H, s, 10-H), 7.56-7.34 (7 H, m, arH, 6-H and 7-H), 7.08 (1 H, t, J7, 8-H), 5.42 (2 H, s, C$\underline{H}_2$Ph) and 2.92 (6 H, s, 3-CH$_3$ and 4-CH$_3$); m/z (%) 368(74,M$^+$), 354(10), 260(100), 246(13), 231(20) and 91(31).

The pyrrolo[3,2-b]carbazole (0.166 g, 45%) was also obtained from the reaction of indole and the 4-acetyl-5-(ethoxymethyl)pyrrole.

c) Ethyl 8-methoxy-3,4-dimethylpyrrolo[3,2b]carbazole-2-carboxylate

Was obtained from the reaction of 5-methoxyindole and the 5-acetoxymethyl-4-acetyl pyrrole, it had m.p. 119°–122° C. (Found: C,71.6; H, 6.0; N, 8.05. $C_{20}H_{20}N_2O_3$ requires C, 71.4; H, 5.99; N, 8.33%); $\delta_H([^2H_6]$-DMSO) 11.20 (1 H, s, 1-NH), 10.38 (1 H, s, 5-NH), 7.85(1 H, s, 10-H), 7.62 (1 H, d, J 2.5, 9-H), 7.31 (1 H, d, J9, 6-H), 7.01 (1 H, dd, J9 and 2.5, 7-H), 4.38 (2 H, q, OC$\underline{H}_2$CH$_3$), 3.88 (3 H, s, OCH$_3$), 2.89 and 2.87 (2×3 H, 2×S, 3-CH$_3$ and 4-CH$_3$) and 1.39 (3 H, t, OCH$_2$C$\underline{H}_3$); m/z (%) 336(60,M$^+$), 290(100), 275(5), 262(4), 247(23), 219(8) and 145(9).

d) Benzyl 8-methoxy-3,4-dimethylpyrrolo[3,2-b]carbazole-2-carboxylate (0.139 g, 35%) was obtained from the reaction of 5-methoxy indole and the 5-acetoxymethyl-4-acetylpyrrole, it had m.p. 212°–215° C. (Found: C, 75.4; H, 5.55; N, 6.95. $C_{25}H_{22}N_2O_3$ requires C, 75.4; H, 5.57; N,7.03%); $\delta_H([^2H_6]$-DMSO) 11.29 (1 H, s, 1-NH), 10.38 (1 H, s,5-NH), 7.88 (1 H,s,10-H), 7.65 (1 H, d, J2.5, 9-H), 7.58-7.36 (5 H, m, ArH), 7.32 (1 H, d, J9, 6-H), 7.02 (1 H, dd, J9 and 2.5, 7-H), 5.43 (2 H, s, C$\underline{H}_2$Ph), 3.88 (3 H, s, OCH$_3$), 2.92 (3 H, s, 4-CH$_3$) and 2.89 (3 H, s, 3-CH$_3$); m/z (%) 398(73,M$^+$), 290(100), 262(10), 247(15), 219(7), and 91(17).

e) Ethyl 8-fluoro-3,4-dimethylpyrrolo[3,2-b]carbazole-2-carboxylate (0.131 g, 40.5%) was obtained from the reaction of 5-fluoroindole and the 5-acetoxymethyl-4-acetylpyrrole, it had m.p. 231°–234° C. (Found: C, 70.5; H, 5.3; N, 8.4. $C_{19}H_{17}FN_2O_2$ requires C, 70.4;,H,5.28; N, 8.64%); $\delta_H[^2H_6]$-DMSO) 11.27 (1 H, s, 1-NH), 10.64 (1 H, s, 5-NH), 7.93 (1 H, dd, J9 and 2.5, 9-H), 7.88 (1 H, m, 10-H), 7.36(1 H, dd, J9 and 6,6-H), 7.19 (1 H, dt, J9 and 2.5, 7-H), 4.36 (2 H, q, OC$\underline{H}_2$CH$_3$), 2.88 (6 H, s, 3-CH$_3$ and 4-CH$_3$) and 1.37 (3 H, t, OCH$_2$C$\underline{H}_3$); m/z (%) 324(50,M$^+$) 278(100), 250(31), 220(10), 139(8), 125(7) and 111(8)

f) Benzyl 8-fluoro-3,4-dimethylpyrrolo[3,2-b]carbazole-2-carboxylate (0.155 g, 40%) was obtained from 5-fluoroindole and the 5-acetoxymethyl-4-acetylpyrrole, it had m.p. 217°–219° C. (Found: C, 74.6; H, 4.95; N, 7.3. $C_{24}H_{19}FN_2O_2$ requires C, 74.6; H, 4.96; N, 7.25); $\delta_H([^2H_6]$-DMSO) 11.36 (1 H, s, 1-NH), 10.86 (1 H, s, 5-NH), 7.94 (1 H, dd, J9 and 2.5, 9-H), 7.89 (1 H, s, 10-H), 7.56-7.38 (5 H, m, ArH), 7.39 (1 H, dd, J9 and 4,6-H, 7.21 (1 H, dt, J9 and 2.5, 7-H), 5.42 (2 H, s, C$\underline{H}_2$Ph), 2.91 (2×3H, 2×S, 3-CH$_3$ and 4-CH$_3$); m/z (%) 386(68,M$^+$), 278(100), 249(22) and 91(43).

g) Ethyl 3,46-trimethylpyrrolo[3,2-b]carbazole-2-carboxylate (0.206 g, 64.4%) was obtained from the reaction of 7-methylindole and the 5-acetoxymethyl-4-acetylpyrrole, it had m.p. 230° C. (decomp.) (Found: C, 74.9; H, 6.25; N, 8.65. $C_{20}H_{20}N_2O_2$ requires C, 75.0; H, 6.29; N, 8.74%); $\delta_H([^2H_6]$-DMSO) 11.20 (1 H, s,1-NH), 10.11 (1 H, s, 5-NH), 7.89(1 H, d, J7.5, 9-H), 7.84 (1 H, s, 10-H), 7.18 (1 H, d, J7.5, 7-H), 7.01 (1 H, t, J7.5, 8-H), 4.37 (2 H, q, OC$\underline{H}_2$CH$_3$), 2.98 (3 H, s, 4-CH$_3$), 2.91 (3 H, s, 3-CH$_3$), 2.58 (3 H, s, 6-CH$_3$) and 1.34 (3 H, t, OCH$_2$C$\underline{H}_3$); m/z (%) 320(54, M$^+$), 274(100), 246(30), 230(5), 137(9), 123(7) and 109(6).

h) Benzyl 3,46-trimethylpyrrolo[3,2-b]carbazole-2-carboxylate (0.167 g. 43.7%) was obtained from the reaction of 7-methylindole and the 5-acetoxymethyl-4-acetylpyrrole, it had m.p. 222° C. (decomp.) (Found: C, 78.5; H, 5.9; N.7.25. $C_{25}H_{22}N_2O_2$ requires C, 78.5; H, 5.80; N, 7.33%); $\delta_H([^2H_6]$-DMSO) 11.27 (1 H, s, 1-NH), 10.11 (1 H, s, 5-NH), 7.89 (1 H, d, J7, 9-H), 7.85 (1 H, s, 10-H), 7.56-7.35 (5 H, m, ArH), 7.18 (1 H, d, J7, 7-H), 7.08 (1 H, t, J, 8-H), 5.43 (2 H, s, C$\underline{H}_2$Ph), 2.99 (3 H, s, 4-CH$_3$), 2.93 (3 H, s, 3-CH$_3$) and 2.59 (3 H, s, 6-CH$_3$); m/z (%) 382(71,M$^+$) 274(100), 246(19) and 91(22).

i) Benzyl 3-(2-methoxycarbonylethyl)-4-methylpyrrolo[3,2-b]carbazole-2-carboxylate (0.230 g, 52.3%) was obtained from indole and the 5-acetoxymethyl-4-acetylpyrrole, it had m.p. 211°–213° C. (Found: C, 73.7; H, 5.6; N, 6.2. $C_{27}H_{24}N_2O_4$ requires C, 73.6; H, 5.49; N, 6.36%); $\delta_H([^2H_6]$-DMSO) 11.51 (1 H, s, 1-NH), 10.71 (1 H, s, 5-NH), 8.75 (1 H, d, J7.5, 9-H). 7.92 (1 H, s, 10-H), 7.57-7.44 (7 H, m, ArH, 6-H and 7-H), 7.18 (1 H, t, J7.5, 8-H), 5.43 (2 H, s, C$\underline{H}_2$Ph), 3.63 (3 H,s,OCH$_3$), 3.59 (2 H, partially obscured, t, C$\underline{H}_2$CH$_2$CO), 2.88 (3 H, s, 4-CH$_3$) and 2.65 (2 H, t, CH$_2$CO); m/z(%) 440(100,M$^+$), 332(20), 290(47), and 91(57).

j) Ethyl 3,4,5-trimethylpyrrolo[3,2-b]carbazole-2-carboxylate (0.140 g, 16%) was obtained from the reaction (2.65 mmol scale) between N-methylindole and the 5-acetoxymethyl-4-acetylpyrrole, it had m.p. 208° C. (decomp.) (Found: C, 75.12; H, 6.40; N, 8.69, $C_{20}H_{20}N_2O_2$ requires C, 74.98; H, 6.29; N, 8.74%); $\delta_H([^2H_6]$-DMSO) 11.28 (1 H, s, 1-NH), 8.08 (1 H, d, J7.9, 9-H), 7.88 (1 H, s, 10-H), 7.44 (2 H, m, 6-H, 7-H), 7.07-7.17 (1 H, m, 8-H), 4.36 (2 H, q, C$\underline{H}_2$CH$_3$), 4.01 (3 H, s, 5-CH$_3$), 3.13 (3 H, s, 4-CH$_3$), 2.90 (3 H, s, 3-CH$_3$), and 1.38 (3 H, t, CH$_2$C$\underline{H}_3$); m/z (%) 320(72,M$^+$), 274(100), 245(16), 149(28) and 137 (12); $\nu_{max}$(KBr Disc)/cm$^{-1}$ 3329 and 1670.

k) Benzyl 3,4,5-trimethylpyrrolo[3,2-b]carbazole-2-carboxylate (0.220 g, 57%) was obtained from the reaction between N-methyl indole and the 5-acetoxymethyl-4-acetylpyrrole in toluene at 55° C., catalysed by toluene-4-sulphonic acid, it had m.p. 228°–229° C. (Found: C, 77.17; H, 5.73; N, 7.09. C$_{25}$H$_{22}$N$_2$O$_2$.0.33 H$_2$O requires C, 77.31; H, 5.88; N, 7.21%); $\delta_H([^2H_6]$-DMSO) 11.28 (1 H, s, 1-NH), 8.03 (1 H, d, J7.5, 9-H), 7.88 (1 H, s, 10-H), 7.56-7.34 (7 H, m, ArH, 6-H, 7-H), 7.15-7.07 (1 H, m, 8-H), 5.40 (2 H,s, C$\underline{H}_2$Ph), 4.02 (3 H, s, 5-CH$_3$), 3.14 (3 H, s, 4-CH$_3$) and 2.91 (3 H, s, 3-CH$_3$); m/z (%) 382(72,M$^+$), 291(4), 274(100) and 91(34); $\nu_{max}$(KBr Disc)/cm$^{-1}$ 3337 and 1674.

l) Ethyl 1,3,4-trimethylpyrrolo[3,2-b]carbazole-2-carboxylate (0.060 g, 7%) was obtained from the reaction (2.5 mmol scale) between indole and the 5-acetoxymethyl-4-acetylpyrrole, it had m.p. 188°–189° C (Found: C, 74.86; H, 6.32; N, 8.65%), C$_{20}$H$_{20}$N$_2$O$_2$ requires C, 75.98; H, 6.29; N, 8.74%); $\delta_H([^2H_6]$-DMSO) 10.66 (1 H, s, 5-NH), 8.14 (1 H, d, J7.7, 9-H), 8.03 (1 H, s, 10-H), 7.45-7.31 (2 H, m, 6-H, 7-H), 7.06-7.15 (1 H, m, 8-H), 4.38 (2 H, q, C$\underline{H}_2$CH$_3$), 3.98 (3 H, s, 1-CH$_3$), 2.91 (3 H, s, 4-CH$_3$), 2.83 (3 H, s, 3-CH$_3$) and 1.38 (3 H, t, CH$_2$C$\underline{H}_3$); m/z (%) 320(M$^+$,100), 306(10), 292(30), 247(8) and 231(10); $\nu_{max}$(KBr Disc)/cm$^{-1}$ 3385 and 1657.

m) Benzyl 1,3,4-trimethylpyrrolo[3,2-b]carbazole-2-carboxylate (0.240 g, 28%) was obtained from the reaction (2.7 mmol scale) between indole and the 5-acetoxymethyl-4-acetylpyrrole, it had m.p. 186°–187° C. (Found: C, 78.63; H, 5.83; N, 7.32, C$_{25}$H$_{22}$N$_2$O$_2$ requires C, 78.51; H, 5.80; N, 7.32%); $\delta_H([^2H_6]$-DMSO) 10.66 (1 H, s, 5-NH), 8.14 (1 H, d, J7.4, 9-H), 8.02 (1 H, s, 10-H), 7.56-7.31 (7 H, m, ArH, 6-H, 7-H), 7.06-7.15 (1 H, m, 8-H), 5.41 (2 H, s, C$\underline{H}_2$Ph), 3.98 (3 H, s, 1-CH$_3$), 2.90 (3 H, s, 4-CH$_3$) and 2.83 (3 H, s, 3-CH$_3$); m/z (%) 3.82(M$^+$,100), 338(10), 291(44), 247(18) and 231(10); $\nu_{max}$(KBr Disc)/cm$^{-1}$ 3443 and 1697.

n) Ethyl 1,3,4,5,-tetramethylpyrrolo[3,2-b]carbazole-2-carboxylate (0.220 g, 30%) was obtained from the reaction (2.2 mmol scale) between N-methylindole and the 5-acetoxymethyl-4-acetylpyrrole, it had m.p. 165.5°–167° C. (decomp.) (Found: C, 75.50: H, 6.65; N, 8.30, C$_{21}$H$_{22}$N$_2$O$_2$ requires C, 75.47; H, 6.63; N, 8.38%); $\delta_H([^2H_6]$-DMSO) 8.15 (1 H, d, J7.5, 9-H), 8.07 (1 H, s, 10-H), 7.50-7.38 (2 H, m, 6-H, 7-H), 7.09-7.19 (1 H, m, 8-H), 4.38 (2 H, q, C$\underline{H}_2$CH$_3$), 4.03 (3 H, s, 5-CH$_3$), 3.96 (3 H, s, 1-CH$_3$), 3.14 (3 H, s, 4-CH$_3$), 2.84 (3 H, s, 3-CH$_3$) and 1.39 (3 H, t, CH$_2$C$\underline{H}_3$); m/z (%) 334(100,M$^+$), 306(18) and 245(6); $\nu_{max}$(KBr Disc)/cm$^{-1}$ 1690 and 1528.

o) Benzyl 1,3,4,5-tetramethylpyrrolo[3,2-b]carbazole-2-carboxylate (0.070 g, 13%) was obtained from the reaction (1.4 mmol scale) between N-methylindole and the 5-acetoxymethyl-4-acetylpyrrole, it had m.p. 196°–198° C. (Found: c, 78.45; H, 6.16; N, 6.94, C$_{26}$H$_{24}$N$_2$O$_2$ requires C, 78.76; H, 6.10; N, 7.07%); $\delta_H([^2H_6]$-DMSO) 8.15 (1 H d, J7.8,9-H), 8.07 (1 H, s, 10-H), 7.59-7.29 (7 H, m, ArH, 6-H, 7-H), 7.10-7.20 (1 H, m, 8-H), 5.42 (2 H, s, C$\underline{H}_2$Ph), 4.03 (3 H, s, 5-CH$_3$), 3.97 (3 H, s, 1-CH$_3$), 3.13 (3 H, s, 4-CH$_3$) and 2.83(3 H, s, 3-CH$_3$); m/z (%) 396(100,M$^+$), 305(38), 245(16) and 235(10) ;$\nu_{max}$KBr Disc)/cm$^{-1}$ 1696 and 1529.

p) Benzyl 3,4-dimethyl-5-(4-toluenesulphonyl)pyrrolo[3,2-b]carbazole-2-carboxylate (0.012 g, 4%) was obtained from the reaction (0.6 mmol scale) between N-(4-toluenesulphonyl)indole and the 5-acetoxymethyl-4-acetylpyrrole, it had m.p. 270° C. (Found: C, 70.83; H, 5.01; N, 5.23, C$_{31}$H$_{26}$N$_2$O$_4$S requires C, 71.24; H, 5.01; N, 5.36%); $\delta_H([^2H_6]$-DMSO) 11.58 (1 H, s, N-H), 8.28-8.08 (3 H, m, 6-H, 9-H, 10-H), 7.66-7.21 (11 H, m, ArH, TsH, 7-H, 8-H), 5.40 (2 H, s, CH$_2$Ph), 3.04 (3 H, s, 4-CH$_3$), 2.88 (3 H, s, 3-CH$_3$) and 2.20 (3 H, s, Ts-CH$_3$); m/z (%) 525(30,(M+1), 446(20), 367(30), 348(56), 33(100), 295(30) and 274(90); $\nu_{max}$(KBr Disc)/cm$^{-1}$ 3558 and 1666.

q) Ethyl 7-acetoxy-3,4-dimethyl-6-methoxypyrrolo[3,2-b]carbazole-2-carboxylate (7%) obtained from the reaction between 6-acetoxy-7-methoxyindole and the 5-acetoxymethyl-4-acetylpyrrole, it had m.p. 241°–244° C. $\delta_H$ (CDCl$_3$) 8.59 (1H, s, br, NH), 7.78 (1H, s, br, NH), 7.76 (1H, s, 10-H), 7.74 (1H, d, J8, 9-H), 6.88 (1H, d, J8, 8-H), 4.44 (2H, q, CH$_2$CH$_3$), 4.04 (3H, s, 6-OCH$_3$), 2.96 and 2.92 (2×3H, 2×s, 4-CH$_3$ and 3-CH$_3$), 2.42 (3H, s, 7-CH$_3$COO) and 1.46 (3H, t, CH$_2$CH$_3$); m/z (%) 394 (100, M$^+$), 352 (47), 348 (33), 306 (87), 263 (21) and 87 (73) $\nu_{max}$ (Nujol)/cm$^{-1}$ 3413, 3341, 1739 and 1675; $\nu_{max}$ (MeOH)/nm 405, 386, 339, 325, 305, 269, 240 and 226. (Found: M, 394, 1529. C$_{22}$H$_{22}$N$_2$O$_5$ requires 394.1529).

r) Ethyl 9-methoxy-3,4,5-trimethylpyrrolo[3,2-b]carbozole-2-carboxylate obtained from the reaction between 4-methoxy-1-methylindole and the 5-acetoxymethyl-4-acetylpyrrole, it had m.p. 263°–266° C. (Found: C, 71.84; H, 6.34; N, 7.91. C$_{21}$H$_{22}$N$_2$O$_3$ requires C, 71.98; H, 6.33; N, 7.99%; $\delta_H$ (CCDl$_3$) 8.60 (1H, s, br, NH), 8.15 (1H, s, 10-H), 7.40 (1H, t, J8, 7-H), 6.95 (1H, d, J8, 6-H), 6.66 (1H, d, J8, 8-H), 4.43 (2H, q, OCH$_2$CH$_3$), 4.10 and 4.04 (2×3H, 2×s, N-CH$_3$ and OCH$_3$), 3.19 (3H, s, 4-CH$_3$), 2.98 (3H, s, 3-CH$_3$) and 1.46 (3H, t, OCH$_2$CH$_3$); m/z (%) 350 (74, (M$^+$), 304 (100), 276 (17), 223 (10) and 152 (19).

s) Benzyl 8-chloro-3,4-dimethylpyrrolo[3,2-b]carbazole-2-carboxylate (0.069 g; 17%) was obtained from the reaction between 5-chloroindole and the 5-acetoxymethyl-4-acetylpyrrole, it had m.p. 215°–220° C. (decomp.). (Found: C, 71.42; H, 4.96; N, 7.11, C$_{24}$H$_{19}$ClN$_2$O$_2$ requires C, 71.55; H, 4.75; N, 6.95%); $\delta_H$ ($^2$[H]$_6$-DMSO) 11.39 (1H, s, 1-NH), 10.84 (1H, s, 5-NH), 8.17 (1H, s, 9H), 7.93 (1H, s, 10-H), 7.54 (1h, d, J7, 7-H), 7.48–7.34 (6H), m, ArH and 6-H), 5.42 (2H, s, CH$_2$Ph) and 2.88 (6H, s, 3-CH$_3$ and 4-CH$_3$); m/z (%) 402 (30, m$^+$), 358(5), 294 (65), 267 (25) and 91 (100). The crystallization liquors were submitted to flash chromatography on silica. Elution with ethyl acetate/light petroleum yielded further title compound which was crystallised from ethyl acetate (0.030 g; 7%) and 3-(3'-acetyl-5'-benzyloxycarbonyl-4'-methylpyrrol-2'-ylmethyl)-5-chloroindole as cream coloured crystals (0.152 g; 36%) m.p. 141°–143° C. (Found: C, 68.20; H, 5.18; N, 6.60; C$_{24}$H$_{21}$ClN$_2$O$_3$ requires C, 68.49; H, 5.03; N, 6.65); $\delta_H$ (CDCl$_3$) 8.72 (1H, s, 1'-NH), 8.26 (1H, s, 1-NH), 7.38 (1H, d, J2, 4-H), 7.35 (6H), m, ArH and 6-H), 7.18 (1H, dd, J8 and 2, 2-H), 7.09 (1H, d, J2, 2-H), 5.23 (2H, s, CH$_2$Ph), 4.39 (2H, s, 3-CH$_2$), 2.64 (3H), s, 4'-CH$_3$) and 2.52 (3H, s, CH$_3$CO); m/z (%) 420 (20, M$^+$), 405 (10), 311 (20), 151 (15) and 91(100).

t) Ethyl 3,4-dimethyl-8-hydroxypyrrolo[3,2-b]carbazole-2-carboxylate

Obtained from the reaction between 5-hydroxyindole and the 5-acetoxymethyl-4-acetylpyrrole and crystallised from methanol, it had m.p. 250° C. (decomp.) $\delta_H[^2H_6]$-DMSO) 11.11 (1H, s, 1-NH), 10.21 (1H, s, 5-NH), 8.83 (1h, s, OH), 7.73 (1H, s, 10-H), 7.37 (1H, d, J2.5, 9-H), 7.21 (1H, d, J8, 6-H), 6.87 (1H, dd, J8 and 2.5, 9-H), 7.21 (2H, q, OCH$_2$CH$_3$), 2.87 (3H, s, 4-CH$_3$), 2.84 (3H, s, 3-CH$_3$) and 1.38 (3H, t, OCH$_2$CH$_3$); m/z (%) 322 (69, M$^+$), 276 (100), 248 (24), 220(3) and 138 (15); (Found: M$^+$, 322. 1322 C$_{19}$H$_{18}$N$_2$O$_3$ requires M, 322. 1317). Also isolated from the reaction was 3-(3'-acetyl-5'-ethoxycarbonyl-4'-methylpyrrol-2'-ylmethyl)-5-hydroxyindole, it had m.p. 99°–102° C. (Found: C, 66.89; H, 6.17; N, 8.03. C$_{19}$H$_{20}$N$_2$O$_4$ requires C, 67.04; H, 5.92; N, 8.23%) $\delta_H$(CDCl$_3$) 8.84 (1H, s, 1'-NH), 8.14 (1H, s, 1-NH), 7.20 (1H, d, J8, 7-H), 7.10 (1H, d, J 2.5, 2-H), 6.81 (1H, d, J1.5, 4-H), 6.79 (1H, dd, J1.5 and 8, 6-H), 5.60 (1H, s, br, 5-OH), 4.31 (1H, s, CH$_2$), 4.21 (2H, q, OCH$_2$CH$_3$), 2.58 (3H, s, 4'-CH$_3$) 2.48 (3H, s, 3'-COCH$_3$) and 1.27 (3H, t, OCH$_2$CH$_3$); m/z (%) 340 (100, M$^+$), 325 (44), 293 (21), 279 (35), 266 (35), 251 (31), 223 (25), 196 (5), 147 (20) and 133 (36).

u) Benzyl 3,4-dimethyl-7-fluoropyrrolo[3,2-b]carbazole-2-carboxylate and Benzyl 3,4-dimethyl-8-fluoro-pyrrolo[2,3-b]carbazole-2-carboxylate obtained as a mixture of isomers from the reaction between 6-fluoroindole and the 5-acetoxymethyl-4-acetylpyrrole. Chromatographic separation yielded the [3,2-b]isomer (0.139 g, 36%) m.p. 205° C. (decomp.) $\delta_H$([$^2$H$_6$]-DMSO) 11.32 (1H, s, 1-NH), 10.85 (1H, s, 5-NH), 8.08 (1H, dd, J9 and 6, 9-H), 7.86 (1H, s, 10-H), 7.57–7.35 (5H, m, ArH), 7.12 (1H, dd, J10 and 2, 6-H), 6.90 (1H, dt, J9 and 2, 8-H), 5.43 (2H, s, CH$_2$Ph), 2.91 (3H, s, 3-CH$_3$) and 2.90 (3H, s, 4-CH$_3$); m/z (%) 386 (55, M$^+$),342(5), 295 (4), 278(100), 249(45), 236(20), 222 (25) and 91 (95); (Found: MH$^+$, 387. 1509. C$_{24}$H$_{20}$FN$_2$O$_2$ requires 387.1509); and the [2,3-b]isomer m.p. 190°–193° C. $\delta_H$(CDCl$_3$) 8.54 (1H, s, br, 1-NH), 8.10 (1H, d, J9 and 6, 5-H), 7.87 (1H, s, br, 9-NH), 7.51–7.34 (5H, m, ArH), 7.34 (1H, s, 10-H), 7.22 (1H, dd, concealed by 10-H, 8-H), 6.93 (1H, dt, J2 and 9, 6-H), 5.41 (2H, s, CH$_2$Ph), 3.20 (3H, s, 4-CH$_3$) and 3.00 (3H, s, 3-CH$_3$); m/z (%) 386 (100, M$^+$), 295 (12), 278 (96), 250 (27), 236 (7), 222(8) and 91 (59(Found: M$^+$, 386.1433. C$_{24}$H$_{19}$FN$_2$O$_2$ requires 386.1431).

v) Ethyl 3,4-dimethyl-7-fluoropyrrolo[3,2-b]carbazole-2-carboxylate and Ethyl 3,4-dimethyl-8-fluoropyrrolo[2,3-b]carbazole-2-carboxylate obtained as a mixture of isomers from the reaction between 6-fluoroindole and the 5-acetoxymethyl-4-acetylpyrrole. Chromatographic separation yielded the [3,2-b]isomer which was crystallised from dichloromethane, m.p. 231°–234° C. (Found: C, 70.45; H, 5.53; N, 8.66, C$_{19}$H$_{17}$FN$_2$O$_2$ requires C, 70.36, H, 5.28; N, 8.64%); $\delta_H$([$^2$H$_6$]-DMSO) 11.27 (1H, s, br, 1-NH), 10.82 (1H, s, br, 5-NH), 8.90 (1H, dd, J9 and 6, 9-H), 7.85 (1H, s, 10-H), 7.12 (1H, dd, J10 and 2, 6-H) 6.89 (1H, dt, J2 and 9, 8-H), 4.37 (2H, q, OCH$_2$CH$_3$) 2.89 (6H, s, 4-CH$_3$), 1.39 (3H, t, OCH$_2$CH$_3$): m/z (%) 324 (60, M$^+$), 278 (100), 250 (34), 222 (10) and 139 (7); Found; M$^+$, 324.1267. C$_{19}$H$_{17}$FN$_2$O$_2$ requires 324.1274); and the [2,3-b]isomer m.p. 262°–265° C.; $\delta_H$([$^2$H$_6$]-DMSO) 11.14 (1H, s, br, 1-NH), 11.06 (1H, s, br, 9-NH), 8.12 (1H, dd J 6 and 9, 5-H), 7.19 (1H, s, 10-H), 7.15 (1H, dd J10 and 2, 8-H), 6.92 (1H, dt, J2 and 9, 6-H), 4.36 (2H), q, OCH$_2$CH$_3$), 3.13 (3H), s, 4-CH$_3$), 2.93 (3H, s, 3-CH$_3$), and 1.39 (3H, t, OCH$_2$CH$_3$); m/z (%) 324 (72, M$^+$), 278 (100), 250 (39), 222 (9), 139(6), and 125(7); Found: M$^+$, 324.1280. C$_{19}$H$_{17}$FN$_2$O$_2$ requires 324.1274).

w) Ethyl 3,4-dimethyl-9-hydroxypyrrolo[3,2-b]carbazole-2-carboxylate and Ethyl 3,4-dimethyl-5-hydroxypyrrolo[3,2-b]carbazole-2-carboxylate obtained as a mixture of isomers from the reaction between 4-hydroxyindole and the 5-acetoxymethyl-4-acetylpyrrole. Chromatographic separation yielded the [3,2-b]isomer which was crystallised from ethyl acetate/light petroleum, m.p. 260°–262° C. (decomp.) $\delta_H$([$^2$H$_6$]-DMOS) 11.13 (1H, s, 1-NH), 10.56 (1H, s, 5-NH), 10.00 (1H, s, OH), 8.02 (1H, s, 10-H), 7.12 (1H, t, J7.5, 7-H), 6.83 (1H, d, J7.5, 6-H), 6.48 (1H, d, J7.5, 8-H), 4.39 (2H, q, OCH$_2$CH$_3$), 2.87 (3H, s, 4-CH$_3$), 2.85 (3H, s, 3-CH$_3$) and 1.38 (3H, t, OCH$_2$CH$_3$); m/z (%) 322 (61, M$^+$), 276 (100), 248 (20), 219 (5) and 138 (11); (Found: M$^+$, 322.1305. C$_{19}$H$_{18}$N$_2$O$_3$ requires 322.1317); and the [2,3-b]isomer which was crystallised from ethyl acetate, m.p. 251°–254° C. (decomp.) $\delta_H$([$^2$H$_6$]-DMSO) 10.95 (1H, s, 1-NH), 10.85 (1H, s, 9-H), 9.89 (1H, s, OH), 7.08 (1H, t, J7.5, 7-H), 7.07 (1H, s, 10-H), 6.77 (1H, d, J7.5, 8-H), 6.52 (1H, d, J7.5, 7-H), 4.32 (2H, q, OCH$_2$CH$_3$), 3.44 (3H, s, 4-CH$_3$), 2.92 (3H, s, 3-CH$_3$) and 1.37 (3H, t, OCH$_2$CH$_3$); m/z (%) 322 (65, M$^+$), 276 (100), 248 (88), 219 (15), 205(10), 191 (10 178 (5), 165 (5), 138 (10) and 115 (10); (Found: M$^+$, 322.1317. C$_{19}$H$_{18}$N$_2$O$_3$ requires 322.1317).

x) Ethyl 6,9-dimethoxy-3,4-dimethylpyrrole[3,2-b]carbazole-2-carboxylate and Ethyl 5,8-dimethoxy-3,4-dimethylpyrrolo2,3-b]-carbazole-2-carboxylate obtained as a mixture of isomers from the reaction between 4,7-dimethoxyindole and the 5-acetoxymethyl-4-acetylpyrrole. Chromatographic separation yielded the [3,2-b]isomer (13.7%) m.p. 256°–258° C. (Found: C, 68.98; H, 6.23; N, 7.89. C$_{21}$H$_{22}$N$_2$O$_4$ requires C, 68.84; H, 6.05; N, 7.65%). $\delta_H$ (CDCl$_3$) 8.58 (1H, s, br, NH), 8.08 (1H, s, 10-H),7.84 (1H, s, br, NH), 6.82 (1H, d, J8, 7-H), 6.50 (1H, d, J8, 8-H), 4.43 (2H, q, OCH$_2$CH$_3$), 4.05 (3H, s, 9-OCH$_3$), 3.98 (3H, s, 6-OCH$_3$), 2.96 (3H, s, 4-CH$_3$), 2.92 (3H, s, 3-CH$_3$) and 1.44 (3H, t, OCH$_2$CH$_3$); m/z (%) 366 (73, M$^+$), 326 (100), 305 (11), 290 (11), 277 (23), 262 (15), 183(10), 160 (17), 152 (19) and 131(7); $\nu_{max}$ (Nujol)/cm$^{-1}$ 3474, 3323 and 1674; $\lambda_{max}$ (MeOH)/nm 415, 387, 344, 330(sh), 305(sh), 266, 246 and 220; and the [2,3-b]isomer (9.3%) m.p. 193°–195° C. (Found: C, 69.03; H, 6.29; N, 7.42. C$_{21}$H$_{22}$N$_2$O$_4$ requires C, 68.84, H, 6.05; N, 7.65%); $\delta_H$ (CDCl$_3$) 8.44 (1H, s, br, NH), 8.10 (1H, s, br, NH), 7.06 (1H, s, 10-H), 6.82 (1H, d, J8, 7H), 6.56 (1H, d, J8, 6-H), 4.40 (2H, q, OCH$_2$CH$_3$), 3.98 (3H, s, OCH$_3$), 397 (3H, s, OCH$_3$), 3.42 (3H, s, 4-CH$_3$), 3.00 (3H, s, 3-CH$_3$) and 1.43 (3H, t, OCH$_2$CH$_3$); m/z (%) 366 (100, M$^+$), 320 (82), 292 (20), 277 (24), 262 (10), 183 (14), 160 (28), 131 (3); $\nu_{max}$ (Nujol)/cm$^{-1}$ 3457, 3345 and 1660; $\lambda_{max}$(MeOH)/nm 381, 365, 293, 247 and 219.

y) Ethyl 7-methoxy-3,4-dimethylpyrrole[3,2-b]carbazole-2-carboxylate and Ethyl 7-methoxy-3,4-3,4-dimethylpyrrole [2,3-b]carbazole-2-carboxylate obtained as a mixture of isomers from the reaction between 6-methoxyindole and the 5-acetoxymethyl-4-acetylpyrrole. Flash chromatography on silica, eluting with ethyl acetate/cyclohexane (1:1) yielded the [3,2-b]isomer which was crystallized from ethylacetate/cyclohexane, m.p. 239°–241° C. (decomp.) $\delta_H$([$^2$H$_6$]-DMSO) 11.09 (1H, s, 1-NH), 10.49 (1H, s, 5-NH), 7.91 (1H, d, J 8.7, 9-H), 7.73 (1H, s, 10-H), 6.88 (1H, d, J2.3, 6-H), 6.68 (1H, dd, J 8.7 and 2.3, 8-H), 4.35 (2H, q, OCH$_2$CH$_3$), 3.84 (3H, s, 7-OCH$_3$), 2.87 (3H, s, 3-CH$_3$), 2.86 (3H, s, 4-CH$_3$) and 1.37 (3H, t, OCH$_2$CH$_3$); m/z (%) 336 (84, M$^+$), 290 (100), 262 (32), 247 (16) and 219 (16); $\nu_{max}$ (KBr Disc)/cm$^{-1}$ 3342, 1674 and 1628; and the [2,3-b]isomer which was crystallized from ethyl acetate/cyclohexane, m.p. 260° C. (decomp.) $\delta_H$([$^2H_6$]-DMSO) 10.98 (1H, s, 1-NH), 10.74 (1H, s, 9-H), 8.00 (1H, d, J8.7, 5-H), 7.13 (1H, s, 10-H), 6.87 (1H, d, J2.7, 8-H), 6.70 (1H, dd, J8.7 and 2.7, 6-H), 4.34 (2H, q, OCH$_2$CH$_3$), 3.83 (3H, s, 7-OCH$_3$), 3.10 (3H, s, 4-CH$_3$), 2.91 (3H, s, 3-CH$_3$) and 1.37 (3H, t, OCH$_2$CH$_3$); m/z (%) 336 (56, M$^+$), 290 (70), 262 (26), 145 (16), 129 (14); $v_{max}$ (KBr Disc)/cm$^{-1}$ 3379, 3339 and 1663.

z) Ethyl 3-ethyl-4-methylpyrrole[3,2-b]carbazole-2-carboxylate (0.956 g, 27%) was obtained from the reaction (11 mmol scale) between indole and the ethyl 5-acetoxymethyl-4-acetyl-3-ethylpyrrole-2-carboxylate, after recrystallization from toluene, it had m.p. 248°–249° C. (decomp.) (Found: C, 74.93; H, 6.35; N, 8.60. C$_{20}$H$_{20}$N$_2$O$_2$ requires: C, 74.98; H, 6.29; N, 8.74%); $\delta$H([$^2H_6$]-DMSO) 11.27 (1H, s, 1-NH), 10.63 (1H, s, 5-NH), 8.09 (1H, d, J 8, 9-H), 7.93 (1H, s, 10-H), 7.31–7.47 (2H, m, 6-H, 7-H), 7.09 (1H, ddd, J 8, 5.5, 2, 8-H), 4.40 (2H, q, J 7, CO$_2$CH$_2$), 3.37 (2H, q, J 7, 3-CH$_2$), 2.91 (3H, s, 4-CH$_3$), 1.41 (3H, t, J 7, CO$_2$CH$_2$CH$_3$), 1.30 (3H, t, J 7.5, 3-CH$_2$CH$_3$); m/z (%) 320(100, M$^+$), 274(96); $v_{max}$ (KBr disc)/cm$^{-1}$ 3344, 3327, 1680, 1664, 1238.

EXAMPLE 5

Pyrrole[3,2-b]carbazole-2-carboxylic Acids General Procedure.

To a solution of the benzyl pyrrolo[3,2-b]carbazole-2-carboxylate in dry tetrahydrofuran (THF) (10 cm$^3$) was added 10% Pd-on-C (50 mg). The reaction mixture was hydrogenated at one atmos. pressure and room temperature. After uptake of H$_2$ had ceased, the catalyst was removed by filtration through Celite and washed well with THF, and the combined filtrates were evaporated under reduced pressure. Crystallization of the resulting solid from acetone, methyl ethyl ketone or aqueous methanol gave the pyrrolo[3,2-b] carbazole-2-carboxylic acids as yellow crystals.

a) 3,4-Dimethylpyrrolo[3,2-b]carbazole-2-carboxylic acid (0.234 g, 84.3%) m.p. 237° C. (decomp.); $\delta_H$([$^2H_6$]-DMSO) 12.74 (1H, br, s, CO$_2$H), 11.13 (1H, s, 1-NH), 10.60 (1H, s, 5-NH), 8.05 (1H, d, J7.5, 9-H), 7.87 (1H, s, 10-H), 7.42 (1H, d, J7.5, 6-H), 7.36 (1H, t, J7.5, 7-H), 7.08 (1H, t, J7.5, 8-H), 2.92 and 2.91 (2×3H, 2×s, 3-CH$_3$ and 4-CH$_3$); m/z(%) 278(30, M$^+$) 260(39), 234(100), 218(19), 204(8), 167(8) 149 130(10) and 117(25) (Found: M$^+$, 278.1060.C$_{17}$H$_{14}$N$_2$O$_2$ requires M, 278.1055).

b) 8-Fluoro-3,4-dimethylpyrrolo[3,2-b]carbazole-2-carboxylic acid (0.845 g, 85.6%) m.p. 236°–239° C., $\delta_H$([$^2H_6$]-DMSO) 12.80 (1H, br, s, CO$_2$H), 11.19 (1H, s, 1-NH), 10.60 (1H, s, 5-NH), 7.91 (1H, dd, J9 and 2.5, 9-H), 7.86 (1H, s, 10-H), 7.37 (1H, dd, J9 and 4,6-H), 7.20 (1H, dt, J9 and 2,5, 7-H) and 2.89 (6H, s, 2×CH$_3$); m/z (%) 296(51, M$^+$), 278(71), 252(100), 250(37), 236(222(13), 139(22), 125(36) and 111 (28) (Found: M$^+$, 296.0960. C$_{17}$H$_{13}$FN$_2$O$_2$ requires M, 296.0961)

c) 3,4,6-Trimethylpyrrolo[3,2-b]carbazole-2-carboxylic acid (0.065 g, 85%) m.p. 230° C. (decomp.) (Found: C,74.2; H,5.55; N,9.4 %C$_{18}$H$_{16}$N$_2$O$_2$ requires C, 74.0; H, 5.52; N, 9.58%); $\delta_H$([$^2H_6$]-DMSO) 12.80 (1H, br, s, CO$_2$H), 11.01 (1H, s, 1-NH), 10.08 (1H, s, 5-NH), 7.90 (1H, d, J7.5, 9-H), 7.82 (1H, s, 10-H), 7.16 (1H, d, J7.5, 7-H), 7.01 (1H, t, J7.5, 8-H), 2.97 (3H, s, 4-CH$_3$), 2.92 (3H, s, 3-CH$_3$) and 2.58 (3H, s, 6-CH$_3$); m/z(%) 292(72,M$^+$), 274(100), 246(50), 230(11), 137(25), 122(24and 109(30).

d) 3-(2-Methoxycarbonylethyl)-4-methylpyrrolo[3,2-b] carbazole-2-carboxylic acid (0.0673 g, 84.6%) m.p. 255° C. (decomp.) (Found: C, 68.4; H,5.3; N,7.75.C$_{20}$H$_{18}$N$_2$O$_4$ requires C, 68.6; H,5.18; N, 8.00%); $\delta_H$([$^2H_6$]-DMSO) 12.88 (1H, br, s, CO$_2$H), 11.34 (1H,s,1-NH), 10.65 (1H, s, 5-NH), 8.06 (1H, d, J7.5, 9-H), 7.88 (1H, s, 10-H), 7.42 (1H, d, J 7.5, 6-H), 7.36 (1H, t, J7.5, 7-H), 7.07 (1H, t, J7.5, 8-H), 3.66 (3H, s, OCH$_3$), 3.63 (2H, partially obscured t, CH$_2$CH$_2$CO), 2.89 (3H, s, 4-CH$_3$), 2.66 (2H, t, CH$_2$CO); m/z(%) 350(100,M$^+$), 332(17), 306(30), 290(63), 272(22), 259(32) and 233(47).

e) 1,3,4-Trimethylpyrrolo[3,2-b]carbazole-2-carboxylic acid (0.060 g, 44%) m.p. 215°–216° C. (decomp.) (Found: C, 73.69; H, 5.51; N, 9.41; C$_{18}$H$_{16}$N$_2$O$_2$ requires c, 73.95; H, 5.52; N, 9.58); $\delta_H$([$^2H_6$]-DMSO) 12.94 (1H, br, s, COOH), 10.63 (1H, s, 5-NH), 8.13 (1H, d, J 7.9, 9-H), 8.00 (1H, s, 10-H), 7.45–7.30 (2H, m, 6-H, 7-H), 7.14–7.04 (1H, m, 8-H), 3.99 (3H, s, 1-CH$_3$), 2.91 (3H, s, 4-CH$_3$) and 2.85 (3H, s, 3-CH$_3$); m/z (%) 292(95,M$^+$), 275(10), 247(40), 232(30), 180(100) and 135(100); $v_{max}$(KBr Disc)/cm$^{-1}$ 3375, 2930 and 1709.

f) 3,4,5-Trimethylpyrrolo[3,2-b]carbazole-2-carboxylic acid (0.015 g, 18%) m.p. 239°–240° C. (decomp.) (Found: C, 74.11; H, 5.38; N, 9.39; C$_{18}$H$_{16}$N$_2$O$_2$ requires C, 73.95; H, 5.52; N, 9.58; $\delta_H$([$^2H_6$]-DMSO) 11.15 (1H, s, 1-NH), 8.04 (1H, d, J 7.5, 9-H) 7.88 (1H, s, 10-H), 7.48–7.41 (2H, m, 6-H, 7-H), 7.17–7.06 (1H, m, 8-H), 4.03 (3H, s, 5-CH$_3$), 3.16 (3H, s, 4-CH$_3$) and 2.93 (3H, s, 3-CH$_3$); m/z (%) (292(90, M$^+$), 274(75), 232(70), 197(35), 181(60), 149(30) and 130(100); $v_{max}$(KBr Disc/)cm$^{-1}$ 3454, 2926 and 1670.

g) 1,3,4,5-Tetramethylpyrrolo[3,2-b]carboazole-2-carboxylic acid (0.030 g, 32%) m.p. 215°–217° C. (decomp.) (Found: C, 74.44; H, 6.00; N, 9.14; C$_{19}$H$_{18}$N$_2$O$_2$ requires C, 74.49; H, 5.92; N, 9.14); $\delta_H$([$^2H_6$])-DMSO) 12.98 (1H, br, s, COOH), 8.14 (1H, d, J7.6, 9-H), 8.04 (1H, s, 10-H), 7.48–7.38 (2H, m, 6-H, 7-H), 7.18–708 (1H, m, 8-H), 4.01 (3H, s, 5-CH$_3$), 3.97 (3H, s, 1-CH$_3$), 3.12 (3H, s, 4-CH$_3$) and 2.84 (3H, s, 3-CH$_3$); m/z (%) 306(100,M$^+$), 279(25), 232(38), 197(34), 181(80) and 149(25); $v_{max}$(KBr Disc)/cm$^{-1}$ 1935 and 1659.

h) 3,4-Dimethylpyrrolo[3,2-b]carbazole-2-carboxylic acid

The ethyl ester (500 mg, 1.6 mmol) in water (15 cm$^3$) and methanol (35 cm$^3$) was heated to reflux and sufficient methanol to achieve dissolution was added. Caesium carbonate (5.32 g; 16 mmol) was added and the mixture was heated to reflux under nitrogen for 18 h. After cooling, solvent was removed in vacuo to leave approximately 20 cm$^3$ of solution which was brought to pH3 by the addition of 0.1M hydrochloric acid whereupon the title compound precipitated out. Filtration, washing with water and drying under vacuum yielded analytically pure product (437 mg; 96%) which was spectroscopically identical to that obtained in Example 5a.

EXAMPLE 6

Pyrrolo[3,2-b]carbazole-2-carboxylic Acid Esters—General procedure

The pyrrolo[3,2-b]carbazole-2-carboxylic acid (1.0 mmol) and N,N'-carbonyl diimidazole (1.1 mmol) were dissolved in freshly distilled tetrahydrofuran under a nitrogen atmosphere. The resulting suspension was stirred at room temperature for at least one hour, and complete conversion of the acid to the imidazolide intermediate was verified by TLC. The alcohol or phenol (1.5–2.0 mmol, i.e. an excess) was added in one portion, and the resulting mixture was heated to reflux under TLC showed complete consumption of the imidazolide intermediate. The product was obtained by column chromatography on silica, followed by recrystallization.

a) Phenyl 3,4-dimethylpyrrolo[3,2-b]carbazole-2-carboxylate was obtained from the reaction of the imidazolide intermediate with phenol. Chromatography (eluting with 10% acetone/90% petrol) followed by recrystallization from acetone-petrol gave orange crystals (0.230 g, 65%) m.p. >230° C. (decomp.) (Found: C,78.17; H, 5.09; N, 7.77. $C_{23}H_{18}N_2O_2$ requires C, 77.95; H, 5.12; N, 7.90%); $\delta([^2H_6]$-DMSO) 11.55 (1H, s, 1-NH), 10.64 (1H, s, 5-NH), 8.10 (1H, d, J7.5, 9-H), 7.94 (1H, s, 10-H), 7.30–7.58 (7H, m, PhH, 6-H, 7-H), 7.09 (1H, ddd, J 7.5, 5.5, 2, 8-H) and 2.97 and 2.95 (2×3H, 2×s, 3-$CH_3$ and 4-$CH_3$); m/z(%) 355(40, $M^+$); $\nu_{max}$(KBr Disc)/$cm^{-1}$ 3396, 1701 and 1180.

b) [(2-Dimethylamino)ethyl] 3,4-dimethylpyrrolo[3,2-b]carbazole-2-carboxylate was obtained from the reaction of the imidazole intermediate with (2-dimethylamino)ethanol. Chromatography (eluting with 10% methanol/90% DCM) gave a yellow solid (0.350 g, 99%).

Recrystallization of a portion from DCM gave yellow crystals with m.p. 174.0°–175.7° C. (decomp.) (Found: C, 70.46; H, 6.48; N, 11.76. $C_{21}H_{23}N_3O_2.0.15CH_2Cl_2$ requires C, 70.29; H, 6.45; N, 11.55); $\delta_H([^2H_6]$-DMSO) 11.18 (1H, s, 1-NH), 10.60 (1H, s, 5-NH), 8.07 (1H, d, J 8, 9-H), 7.89 (1H, s, 10-H), 7.30–7.43 (2H, m, 6-H, 7-H), 1H, ddd, J 8, 6, 2.5, 8-H), 4.41 (2H, t, J6, $OCH_2$), 2.91 (6H, s, 3-$CH_3$ and 4-$CH_3$), 2.69 (2H, t, J 6.0, $NCH_2$) and 2.27 (6H, s, $N(CH_3)_2$); m/z(%) 350(46, $(M+1)^+$), 261(68) and 133(100); $\nu_{max}$(KBr Disc)/$cm^{-1}$ 3377, 1661 and 1238.

c) [(3-Dimethylamino)phenyl] 3,4-dimethylpyrrolo[3,2-b]carbazole-2-carboxylate was obtained from the 0.95 mmol scale reaction of the imidazolide intermediate with (3-dimethylamino)phenol. Chromatography (eluting with 10% ethyl acetate/90% toluene) followed by recrystallization from ethyl acetate gave yellow crystals (0.272 g, 72%) m.p. 240°–242° C. (decomp.) (Found: C, 75.37; H, 5.71; N, 10.36. $C_{25}H_{23}N_3O_2$ requires C, 75.55; H, 5.83; N, 10.57%; $\delta_H$ ($[^2H_6]$-DMSO) 11.49 (1H, s, 1-NH), (10.64 (1H, s, 5-NH), 8.08 (1H, d, J 8, 9-H), 7.91 (1H, s, 10-H), 7.34–7.48 (2H, m, 6-H, 7-H), 7.27 (1H, t, J 8, 5'-H), 7.10 (1H, ddd, J 8, 6, 2, 8-H), 6.56–6.70 (3H, m, 2'-H, 4'-H, 6'-H), 2.96 (3H, s) and 2.94 (9H,s) (3-$CH_3$,4-$CH_3$, $N(CH_3)_2$); m/z (%) 398(38, $M+1)^+$, 261(25 232(21) and 217(100); $\nu_{max}$(KBr Disc)/$cm^{-1}$ 3350, 1674, 1610 and 1232.

d) (3-Pyridyl) 3,4-dimethylpyrrolo[3,2-b]carbazole-2-carboxylate was obtained from the reaction of the imidazolide intermediate with 3-hydroxypyridine. Chromatography (eluting with 50% ethyl acetate/50% petrol) followed by recrystallization from acetone gave yellow crystals (0.230 g, 65%) with m.p. >270° C. (decomp.) (Found: C, 73.88; H, 4.76; N, 11.50. $C_{22}H_{17}N_3O_2.0.2H_2O$ requires: C, 73.61; H, 4.89; N, 11.71%); $\delta_H([^2H_6]$-DMSO) 11.59 (1H, s, 1NH), 10.65 (1H, s, 5-NH), 8.63 (1H, d, J 2, 2'-H), 8.55 (1H, dd, J 4, 1, 6'-H), 8.10 (1H, d, J 8, 9-H), 7.90 (1H, s, 10-H), 7.86 (1H, ddd, J 8, 3, 1, 5'-H), 7.58(1H, dd, J 8, 5, 4'-H), 7.32–7.45 (2H, m, 6-H, 7-H), 7.09(1H, ddd, J 8, 6, 2, 8-H) and 2.97 and 2.94 (2×3H, 2×s, 3-$CH_3$ and 4-$CH_3$); m/z (%) 356(15, $(M+1)^+$). $\nu_{max}$(KBr Disc)/$cm^{-1}$ 3377, 1715 and 1173.

e) (4-Carbamoylphenyl) 3,4-dimethylpyrrolo[3,2-b]carbazole-2-carboxylate was obtained from the reaction of the imidazolide intermediate with 3-hydroxybenzamide. Recrystallization from ethanol gave a yellow powder, and an impure residue. The latter material was further purified by column chromatography on silica (eluted with 5%) methanol/95% DCM then 10% methanol/90% DCM) followed by recrystallization from ethanol. (0.262 g, 66%) m.p. >250° C. (decomp.) (Found: C, 71.72; H, 4.81; N, 10.26. $C_{24}H_{19}N_3O_3.0.2H_2O$ requires C, 71.88; H, 4.88; N, 10.48%); $\delta_H$ ($[^2H_6]$-DMSO 11.56 (1H, s, 1-NH), 10.63 (1H, s, 5-NH), 7.90–8.12 (5H, m, 9-H, 10-H, 3'-H, 5'-H, amide N-H), 7.33–7.49 (5H, m, 6-H, 7-H, 2'-H, 6'-H, amide N-H), 7.09 (1H, ddd, J 8.5, 6, 1.5, 8-H) and 2.95 and 2.93 (2×3H, 2×s, 3-$CH_3$ and 4-$CH_3$); m/z (%) 398(10, $(M+1)^+$), 279(100); $\nu_{max}$(KBr Disc)/$cm^{-1}$ 3423, 1717, 1695 and 1171.

f) (Pyridyl-4-methyl) 3,4-dimethylpyrrolo[3,2-b]carbazole-2-carboxylate was obtained from the reaction of the imidazolide intermediate with 4-pyridylcarbinol. Chromatography (eluting with ethyl acetate/petrol, gradient 60%, 80%, 100% ethyl acetate, then methanol/ethyl acetate, gradient 10%, 20%) followed by recrystallization from tetrahydrofuran gave orange crystals (0.168 g, 46%) with m.p. >240° C.(decomp.) (Found: C, 72.16; H, 5.12; N, 10.73. $C_{23}H_{19}N_3O_2.0.7H_2O$ requires C, 72.31; H, 5.38; N, 11.00%); $\delta_H([^2H_6]$-DMSO 11.31 (1H, s, 1-NH), 10.62(1H, s, 5-NH), 8.62 (2H, dd, J 4.5, 0.5, 2'-H, 6'-H), 8.08 (1H, d, J 7.5, 9-H), 7.89 (1H, s, 10-H), 7.53(2H, d, J 5.5, 3'-H, 5'-H), 7.32–7.43 (2H, m, 6-H, 7-H), 7.07 (1H, ddd, J 8, 5, 1, 8-H), 5.45 (2H, s, $ArCH_2$) and 2.94 and 2.92 (2×3H, 2×3-$CH_3$ and 4-$CH_3$); m/z (%) 369(27, $(M+1)^+$), 327(70) and 295(100); $\nu_{max}$(KBr Disc)/$cm^{-1}$ 3400, 1709 and 1232.

g) (1,3-Dibenzyloxypropyl-2) 3,4-dimethylpyrrolo[3,2-b]carbazole-2-carboxylate was obtained from the 1.5 mmol scale reaction of the imidazolide intermediate with (1,3-dibenzyloxy-2-propanol). Chromatography (eluting with 20% ethyl acetate/80% toluene then 40% ethyl acetate/60% toluene) followed by recrystallization from ethyl acetate-ether-petrol gave yellow crystals (0.776 g, 97%) m.p. 124.8°–126° C. (decomp.) (Found: C, 76.35; H, 6.07; N, 5.12. $C_{34}H_{32}N_2O_4$ requires C, 76.67; H, 6.06; N, 5.26%; $\delta_H([^2H_6]$-DMSO) 11.18 (1H, s, 1-NH), 10.60 (1H, s, 5-NH), 8.06 (1H, d, J 7.5, 9-H), 7.88 (1H, s, 10-H), 7.22–7.42 (12H, m, 2×$PhH_5$, 6-H, 7-H), 7.07 (1H, ddd, J 8, 6.5,1.5, 8-H), 5.44 (1H, quintet, J 5, 1'-H), 4.60 and 4.53 (2×2H, 2×dd, J 12, 2×$PhCH_2O$), 3.77 (4H, d, J 5.5, $OCH(CH_2)_2$) and 2.91 and 2.89 (2×3H, 2×s, 3-$CH_3$ and 4-$CH_3$); m/z(%) 532(50,$M^+$), 260(65) and 91(100); $\nu_{max}$(KBr Disc)/$cm^{-1}$ 3358, 1681 and 1234.

h) (4-Methylsulphinylphenyl) 3,4-dimethylpyrrolo[3,2-b]carbazole-2-carboxylate was obtained from the reaction of the imidazolide intermediate with 4-methylsulphinylphenol. Chromatography (eluting with ethyl acetate/petrol, gradient 90%, 95%, 98%, 100% ethyl acetate, then 10% methanol/ethyl acetate) followed by recrystallization from tetrahydrofuran gave a yellow powder (0.261 g, 63%) m.p. >230° C. (decomp.) (Found: C, 68.40; H,4.81; N, 6.44. $C_{24}H_{20}N_2O_3S.0.3H_2O$ requires C, 68.32; H, 4.92; N, 6.64%; $\delta_H([^2H_6]$-DMSO) 11.59 (1H, s, 1-NH), 10.68 (1H, s, 5-NH), 8.10 (1H, d, J 8, 9-H), 7.93 (1H, s, 10-H), 7.82(2H, d, J 9.5, 3'-H, 5'H), 7.59 (2H, d, J 9.5, 2'-H, 6'-H), 7.33–7.45 (2H, m, 6-H, 7-H), 7.09 (1H, ddd, J 8, 6, 2.5, 8-H), 2.99 and 2.95 (2×3H, 2×s, 3-$CH_3$ and 4-$CH_3$) and 2.82 (3H, s, $CH_3SO$); m/z (%) 417(2, $M+1^+$), 261(100) and 233(75); $\nu_{max}$(KBr Disc/$cm^{-1}$ 3427, 3288, 1717 and 1200.

i) Methyl 3,4-dimethylpyrrolo[3,2-b]carbazole-2-carboxylate was obtained from the reaction of the imidazolide intermediate with methanol. Chromatography (eluting with 30% ethyl acetate/petrol), followed by recrystallization from ethyl acetate gave a yellow powder (0.188 g, 64%) with m.p. 211°–213° C. (decomp.) (Found: C,74.06, H, 5.49, N,9.42, $C_{18}H_{16}N_2O_2$ requires: C, 73.95; H, 5.52; N, 9.58%); $\delta_H$([$^2H_6$]-DMSO) 11.25 (1H, s, 1-NH), 10.62 (1H, s, 5-NH), 8.08 (1H, d, J 8, 9-H), 7.89 (1H, s, 10-H), 7.33–7.58 (2H, m, 6-H, 7-H), 7.09 (1H, ddd, J 8, 6, 1, 8-H), 3.92 (3H, s, OCH$_3$), 2.92 and 2.91 (2×3H, 2×s, 3-CH$_3$ and 4-CH$_3$); m/z (%) 292(68, M$^+$), 260(100), 232(39); $v_{max}$ (KBr disc)/cm$^{-1}$ 3342, 1684 and 1236.

j) [(2-Methylsulphonyl ethyl]3,4-dimethylpyrrolo[3,2-b]carbazole-2-carboxylate

Was obtained from the reaction of the imidazolide intermediate with (2-methylsulphonyl)ethanol. Chromatography (gradient elution with ethyl acetate/petrol, 30%–100%) followed by recrystallization from acetone gave fine yellow crystals (0.222 g, 58%) with m.p. 255°–257° C. (decomp.) (Found: C, 62.23; H, 5.25; N, 7.08. $C_{20}H_{20}N_2O_4S$ requires C, 62.48; H, 5.24; N, 7.29%); $\delta_H$[$^2H_6$]-DMSO 11.19 (1H, s, 1-H), 10.60 (1H, s, 5-NH), 8.09 (1H, d, J 7.5, 9-H), 7.89 (1H, s, 10-H), 7.32–7.45 (2H, m, 6-H, 7-H), 7.09 (1H, ddd, J 7.5, 5.5, 3, 8-H), 4.69 (2H, t, J 5.5, OCH$_2$), 3.69 (2H, t, J 5.5, SO$_2$CH$_2$), 3.12 (3H, s, SO$_2$CH$_2$), 2.93 (6H, s, 3-CH$_3$ and 4-CH$_3$); m/z (%) 384 (17, M$^+$), 260(13), 59(100); $v_{max\ (KBr\ disc)/cm^{-1}}$ 3387, 1661. 1234.

k) Tert-butyl 3,4-dimethylpyrrolo[3,2-b]carbazole-2-carboxylate

The pyrrolo[3,2-b]carbazole-2-carboxylic acid (0.86 mmol) and triphenylphosphine (0.91 mmol, 1.05 eq.) were dissolved in freshly distilled tetrahydrofuran under a nitrogen atmosphere. Tertiary butanol (2.12 mmol, 2.5 eq.) was added by syringe, and finally diethyl azodicarboxylate (0.95 mmol, 1.1 eq.) was added dropwise over 10 minutes. The resulting suspension was stirred at room temperature for two hours, by which time TLC showed complete consumption of the starting acid. The title compound was obtained from the crude reaction mixture in several stages: column chromatography on silica, eluting with 20% ether/80% petrol then 50% ether/50% petrol; column chromatography on silica (eluting with 25% ether/75% petrol then 40% ether/60% petrol); and finally, recrystallisation from DCM gave yellow powder (0.030 g, 10%0 m.p. 187°–189° C. (decomp.) (Found: C, 73.24; H, 6.53; N, 7.93. $C_{21}H_{22}N_2O_2.0.15CH_2Cl_2$ requires C, 73.18; H, 6.47; N, 8.07%); $\delta_H$([$^2H_6$]-DMSO) 10.95 (1H, s, 1-NH), 10.57 (1H, s, 5-NH), 8.05 (1H, d, J 8, 9-H), 7.88 (1H, s, 10-H), 7.29–7.43 (2H, m, 6-H, 7-H), 7.05 (1H, ddd, J 8, 6, 1, 8-H), 2.89 and 2.87 (2×3H, 2×s, 3-CH$_3$ and 4-CH$_3$) and 1.59 (9H, s, C(CH$_3$)$_3$); m/z (%) 355(62, M+1$^+$), 278(90), 233(38), 126(32), 91(78) and 57(100); $v_{max}$(KBr Disc)/cm$^{-1}$3337, 1664 and 1240.

EXAMPLE 7

Pyrrolo[3,2-b]carbazole-2-carboxylic Acid Amides a) 3,4-Dimethyl-2-(1-imidazolylcarbonyl)pyrrolo[3,2-b]carbazole 3,4-Dimethylpyrrolo[3,2-b]carbazole-2-carboxylic acid (0.280 g, 1.0 mmol) and N,N'-carbonyldiimidazole (0.164 g, 1.0 mmol) were dissolved in freshly distilled tetrahydrofuran (5 cm$^3$) under a nitrogen atmosphere. The resulting suspension was stirred at room temperature for two hours, and completely conversion of the acid to the imidazolide was verified by TLC. The THF was removed and the residue recrystallised from ethyl acetate to give the product as a yellow solid (0.125 g, 38%) m.p. 252° C. (decomp.) (Found: C, 73.17; H, 4.87; N, 16.80, $C_{20}H_{16}N_4O$ requires: C, 73.15; H, 4.91; N, 17.06%); $\delta_H$([$^2H_6$]-DMSO) 11.53 (1H, s, 1-NH), 10.20 (1H), s, 5-NH), 8.30 (1H, s, 2'-H), 8.12 (1H, d, J8, 9-H), 7.94 (1H, s, 10-H), 7.79 (1H, s, 5'-H), 7.33–7.47 (2H, m, 6-H, 7-H), 7.1 (1H, s, 3'-H), 7.09 (1H, ddd, J8, 6, 2, 8-H), 2.95 (3H, s, 3-CH$_3$), 2.73 (3H, s, 4-CH$_3$); m/z (%) 261 (40); $v_{max}$(KBr Disc)/cm$^{-1}$ 3427, 1699 and 1242.

b) Ethyl 3,4-dimethylpyrrolo[3,2-b]carbazole-2-carboxamide 3,4-Dimethylpyrrolo[3,2-b]carbazole-2-carboxylic acid (0.278 g, 1.0 mmol) was dissolved in dimethoxyethane (10 cm$^3$) to give a yellow solution. To this were added diisopropylethylamine (0.260 g, 2.0 mmol), ethylamine hydrochloride (0.245 g, 3.0 mmol) and the tetrafluorborate salt of O-benzotriazolyl-N,N,N',N'-tetramethyluronium (TBTU) (0.482 g, 1.5 mmol) to give a white suspension in the yellow solution. The reaction mixture was stirred at room temperature for 24 h by which time TLC showed no remaining acid. The solvent was removed in vacuo to give a yellow-brown solid. This was subjected to column chromatography on silica eluting firstly with DCM and then with 10% EtOAc/90% DCM to give the ethylamide product as a yellow solid (0.240 g, 79%). To remove a trace impurity, a portion was recrystallized from dichloroethane/petrol to give the compound analytically pure as a yellow powder with m.p. 235° C. (decomp.) (Found: C, 73.21; H, 6.10; N, 13.33. $C_{19}H_{19}N_3O.0.1C_2H_4Cl_2$ requires: C, 73.15; H, 6.20; N, 13.32%); $\delta_H$([$^2H_6$]-DMSO) 10.72 (1H, s, 1-NH), 10.57 (1H, s, 5-NH), 8.09 (1H, d, J8, 9-H), 7.93 (1H, t, J5, amide N-H), 7.83 (1H, s, 10-H), 7.27–7.41 (2H, m, 6-H, 7-H), 7.06 (1H, d, J8, 8-H), 3.35 (2H, q, 7.5, CH$_2$CH$_3$), 2.89 and 2.71 (2×3H, 2×s, 3-CH$_3$ and 4-CH$_3$), 1.18 (3H, t, J 7.5, CH$_2$CH$_3$); m/z (%) 305 (65,M$^+$), 260 (100); $v_{max}$ (KBr Disc)/cm$^{-1}$ 3314, 1603 and 1545.

c) 3,4-Dimethylpyrrolo[3,2-b]carbazole-2-carboxamide 3,4-Dimethylpyrrolo[3,2-b]carbazole-2-carboxylic acid (0.556 g, 2.0 mmol) was dissolved in dimethoxyethane (20 ml) to give a yellow solution. To this were added diisopropylethylamine (0.520 g, 4.0 mmol), ammonium hydrochloride (0.321 g, 6.0 mmol) and the tetrafluorborate salt of O-benzotriazolyl-N,N,N',N', -tetramethyluronium (TBTU) (0.963 g, 3.0 mmol) to give a white suspension in the yellow solution. The reaction mixture was stirred at room temperature for 24 hours, by which time TLC showed no remaining acid. The solvent was removed in vacuo to give a yellow-brown solid. This was subjected to column chromatography on silica (eluting with ethyl acetate/DCM, gradient 10%–30%) to give the amide product as a yellow solid (0.350 g, 63%). To remove a trace impurity, a portion was recrystallised from ethyl acetate/petrol and then purified by preparative HPLC (column size 25 cm×2.12 cm i.d., packed with C$_8$ Zorbax, gradient elution: 5% acetonitrile/95% water to 95% acetonitrile/water; detected at 340 nm) to give a yellow powder with m.p. 240° C. (decomp.) $\delta_H$([$^2H_6$]-DMSO) 10.82 (1H, s, 1-NH), 10.54 (1H, s, 5-NH), 8.08 (1H, d, J 7.5, 9-H), 7.84 (1H, s, 10-H), 7.29–7.43 (4H, m, 6-H, 7-H, NH$_2$), 7.07 (1H, ddd, J 8, 5.5, 2, 8-H), 2.89 and 2.85 (2×3H, 2×s, 3-CH$_3$ and 4-CH$_3$); m/z (%) 277 (62, M$^+$), 260 (100), 232 (44); $v_{max}$ (KBr disc)/cm$^{-1}$ 3317, 1628, 1595; (Found: M+, 277.1205, $C_{17}H_{15}N_3O$ requires 277.1215).

d) Phenyl 3,4-dimethylpyrrolo[3,2-b]carbazole-2-carboxamide 3,4-Dimethylpyrrolo[3,2-b]carbazole-2-carboxylic acid (0.278 g, 1.0 mmol) was dissolved in dimethoxyethane (10 ml) to give a yellow solution. To this were added diisopropylethylamine (0.130 g, 1.0 mmol), aniline (0.190 g, 2.0 mmol) and the tetrafluorborate salt of O-benzotriazolyl-N, N,N',N',-tetramethyluronium (TBTU) (0.482 g, 1.5 mmol) to give a white suspension in the yellow solution. The reaction mixture was stirred at room temperature for 42 hours, by which time TLC showed no remaining acid. The solvent was removed in vacuo to give a yellow solid, which was dissolved in ethyl acetate and the resulting solution washed with water. The organic layer was dried over $MgSO_4$, concentrated, and subjected to column chromatography on silica, eluting with EtOAc/petrol (gradient elution 5%–100%) followed by recrystallisation from acetone to give the phenylamide product as a yellow powder (0.10 g, 30%) with m.p. 260° C. (decomp.) (Found: C, 77.79; H, 5.26; N, 11.64. $C_{23}H_{19}N_3O$ requires: C, 78.16; H, 5.42; N, 11.89%); $\delta_H([^2H_6]$-DMSO) 11.10 (1H, s, 1-NH), 10.59 (1H, s, 5-NH), 9.96 (1H, s, amide N—H), 8.10 (1H, d, J 7.5, 9-H), 7.89 (1H, s, 10-H), 7.79 (2H, d, J 9, 2'-H, 6'-H), 7.29–7.45 (4H, m,6-H, 7-H, 3'-H, 5'-H), 7.00–7.14 (2H, m, 8-H, 4'-H), 2.93 and 2.88 (2×3H, 2×s, 3-$CH_3$); m/z (%) 353 (46, $M^+$), 260 (100); $v_{max}$ (KBr disc)/$cm^{-1}$ 3310, 1614, 1595 and 1317.

e) 3,4-Dimethyl-2-(hydrazinocarbonyl)pyrrolo[3,2-]carbazole

Ethyl 3,4-dimethylpyrrolo[3,2-b]carbazole-2-carboxylate (500 mg) and 95% hydrazine (5 $cm^3$) were stirred and heated at 120° C. for 6 h in a Readi-Vial. The mixture was allowed to stand overnight, cooled in ice and filtered. The resulting yellow solid was washed carefully with water and dried. Yield of title compound 350 mg (73%), no sharp m.p. but decomposes at 285° C. (Found: C, 69;19; H, 5.57; N, 19.38. Calc. for $C_{17}H_{16}N_4O$. 0.1$H_2O$ requires C, 69.42; H, 5.55; N, 19.05%); $\delta_H[^2H_6]$-DMSO) 10.80 (1H, s, exchangeable, NH), 10.55 (1H, s, exchangeable, NH), 9.20 (1H, s, exchangeable, NH), 8.06 (1H, d, J7.5 9-H), 7.81 (1H, s, 10-H), 7.42–7.28 (2H, m, 6-H and 7-H) 7.12–7.01 (1H, m, 8-H, 4.5 (2H, br, s, exchangeable, $NH_2$), and 2.4 and 2.3 (2×s, 4-$CH_3$ and 3-$CH_3$), m/z 293 (M+1)$^+$, FAB)].

EXAMPLE 8

2-Acetyl-3,4-dimethylpyrrolo[3,2-b]carbazole

Step 1

2,4-Diacetyl-3,5-dimethylpyrrole was prepared from acetylacetone and hydroxylamino-O-sulphonic acid according to the procedure of Y. Tamura, S. Kato and M. Ikeda (Chem & Ind., 1971, 767).

Step 2

2-Acetoxymethyl-3,5-diacetyl-4-methylpyrrole

To a stirred mixture of 2,4-diacetyl-3,5-dimethylpyrrole (1.0 g), dichloromethane (35 $cm^3$) and potassium carbonate (7.73 g) at 0°–5° C. was added a solution of sulphuryl chloride (0.79 g) in dichloromethane (15 $cm^3$). The temperature of the mixture was maintained at 0.5° C. during the addition by external cooling and then the mixture was stirred at this temperature until adjudged complete by t.l.c. (ca 2 h). The mixture was then filtered and evaporated to give crude 2-chloromethyl-3,5-diacetyl-4-methylpyrrole. This material was dissolved in acetic acid (10 $cm^3$), sodium acetate (1.83 g) added, and then more acetic acid (10 $cm^3$) added. The mixture was stirred overnight at room temperature, evaporated in vacuo, and the residue stirred with ice-cold water for 2 h. A solid was collected by filtration and the filtrate extracted twice with ethyl acetate. The extracts were dried ($MgSO4$), evaporated and the residue combined with the solid above, to give the crude product. Chromatography on silica eluting with ethyl acetate-hexane (1:1) gave 0.075 g. of pure product as an off-white solid m.p. 112.5°–114.5° C.; m/z 238 ($M^+$+1, FAB), $\delta_H$, $CDCl_3$) 2.16 (3H, s, $OCOCH_3$), 2.50 (3H, s, $CH_3$), 2.53 (3H, s, $CH_3$), 2.62 (3H, s, $CH_3$), 5.38 (2H, s, $OCH_2$).

Step 3

To a solution of 2-acetoxymethyl-3,5-diacetyl-4-methylpyrrole (0.200 g) and indole (0.098 g) in dichloroethane (90 $cm^3$) was added Montmorillonite K10 clay (0.30 g). The mixture was stirred and heated at reflux for 80 h. After cooling the clay was removed by filtration and the filtrate concentrated to ca 20 $cm^3$ in vacuo. The crude product was removed by filtration and then chromatographed on silica. Elution with chloroform-methanol (60:1) yielded 0.08 g of the title compound as a yellow solid m.p. 258°–260° C., m/z (EI) 276 ($M^+$) $\delta_H([^2H_6]$-DMSO) 2.58 (3H, s, $COCH_3$), 2.88 (3H, s, $CH_3$), 2.92 (3H, s, $CH_3$), 7.05 (1H, m, 8-H), 7.38 (2H, m, 6-H, 7-H), 7.85 (1H, s, 10-H), 8.08(1H, J, 8 Hz, 9-H), 10.6 (1H, s, NH), 11.17 (1H, s, NH). (Found: C, 77.0; H, 5.74; N, 9.76; $C_{18}H_{16}N_2O$. 0.14 EtOAc requires C, 77.2; H, 5.98; N, 9.70%.)

EXAMPLE 9

Ethyl 1,5-dihydroindeno[2,1-f]indole-2-carboxylate

Step 1

Ethyl 2-azido-3-fluoren-2-ylacrylate

Sodium (1.7 eq) was added to absolute ethanol stirred under nitrogen at room temperature. When dissolution was complete the reaction was cooled to −10° C. and fluorene-2-carboxaldehyde (1 eq) and ethyl azidoacetate (3 eq) dissolved together in the minimum of tetrahydrofuran were added dropwise. The mixture was stirred at −10° C. for 20 h and then quenched by the addition of water and dichloromethane. The combined organic extracts were dried ($MgSO_4$) and evaporated in vacuo. Flash chromatography yielded the pure product (37%) $v_{max}$ ($CHCl_3$)$cm^{-1}$ 2120 and 1765.

Step 2

Ethyl 2-azido-3-fluoren-2-ylacrylate suspended in dry toluene was heated at reflux for 1 h, and the resulting solution was then evaporated to dryness in vacuo. The resulting mixture of ethyl 1,5-dihydroindino[2,1-f]indole-2-carboxylate and ethyl 1,10-dihydroindino[1,2-g]-indole-2-carboxylate was crystallised from ethanol, thus removing most of the [1,2 g] isomer and leaving the title compound (contained with approximately 30% of the [1,2-g]isomer) in the mother liquors which were evaporated to dryness. $\delta_H$ ($CDCl_3$) 9.11 (1H, s, br, 1-NH), 7.82–7.76 (3H, m), 7.56–7.52 (1H, m), 7.37 (H, dd, J 1 and 7), 7.34–7.28 (1H, m), 7.25 (1H, dd, J 1 and 2), 4.45 (2H, q, $OCH_2CH_3$), 3.97 (2H, s, $CH_2$) and 1.46 (3H, t, $OCH_2CH_3$).

EXAMPLE 10

Effect of compounds of the invention in detransformation ("flattening") assay using HT1080scc2 and HT10801c cell lines.

Cell Lines and Culture Conditions

Transformed and revertant HT1080 sub-lines, HT1080scc2 and HT10801c were obtained from the Institute of Cancer Research, Chester Beatty Laboratories, Fulham Road, London. They were maintained routinely in Dulbecco's Modified Eagle's Medium (DMEM) supplemented with 10% foetal calf serum (FCS) and 1% penicillin/ streptomycin solution containing 10,000 units per ml. All reagents were obtained from Gibco Ltd. Cells were incubated in tissue culture grade plastic vessels at 37° C. in 5 percent $CO_2$ in air.

Assays for Compound Activity

Assays for cell proliferation/cytotoxity were carried out in tissue culture grade 96 well microtitre plates (Costar). Cells in log growth were added to the plates at a concentration of $1\times10^3$ cells per well on day 0 and serially diluted compounds were then added on day 1. Plates were then incubated at 37° C. in 5% $CO_2$ in air for a further 4 days.

For quantitation of cell growth, the methylene blue biomass staining method was used, the test being read on a Multiscan plate reader at wavelength of 620 nm. The morphology of the cells was checked microscopically under phase-contrast immediately before the fixation and staining with methylene blue, and by ordinary light microscopy thereafter. IC50 values for active compounds were obtained using the computer programme, GS1 and dose-response slopes were also plotted.

When compounds were tested for activity in a colony forming assay the methods used were identical to those described earlier except that serially diluted compound was added to the sloppy agar when the test was set up, and replenished at the same concentration on day 7. The test results were read on day 14.

Results

Comparative Growth and Morphology of HT1080scc2 and HT10801c

Growth rates in terms of cell number were similar for both lines to day 4 but thereafter HT1080scc2 cells continued to divide to reach saturation densities approximately 2 to 3 times higher than HT10801c by day 5.

Phenotypic differences between the 2 lines were clearly evident. HT10801c cells displayed a much flatter morphology than the transformed cells and only a few mitotic cells were seen in confluent areas of the cultures. HT1080scc2 cells however continued to divide with numerous mitotic cells visible after confluence.

Grown under anchorage independent conditions in soft agar, HT1080scc2 produced several large colonies whereas HT10801c cells failed to produce any colonies greater than 0.1 mm in diameter.

Effects of Selected Compounds

A number of compounds of the invention were evaluated against the cell lines.

The compounds of the invention exhibited low toxicity with IC50 values in the range 50–100 μM.

Below the results of the "flattening" assay for compounds of cell invention are shown:

| Compound | SCC2 flattening (μM) |
| --- | --- |
| Example 3 | 0.04 |
| Example 4(a) | 0.04 |
| Example 4(b) | 0.04 |
| Example 4(f) | 0.8 |
| Example 4(e) | 0.8 |

| Compound | SCC2 flattening (μM) |
| --- | --- |
| Example 4(h) | 25 |
| Example 4(g) | 25 |

The compounds are effective at achieving "flattening" ie de-transformation, at levels significantly below their toxicity level.

The same compounds were also tested in assays using MCF7 human breast cancer cells, A431 epidermoid carcinoma cells and A285 melanoma cells. In all cases the compounds were effective in the range 1–5 μM.

We claim:
1. A compound of the formula (I)

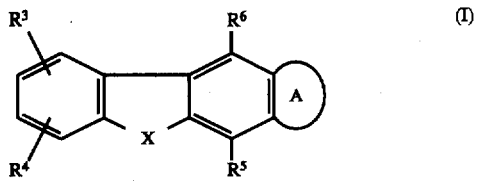

and salts and physiologically functional derivatives thereof, wherein
A is

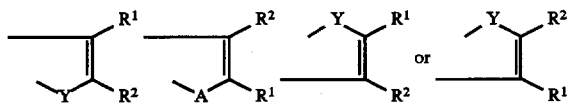

X is $O, S, SO, SO_2, CH_2, CO$ or $NR^7$, wherein $R^7$ is H, $C_{1-10}$ alkyl, aralkyl containing 1 to 4 carbon atoms in the alkyl portion and up to 10 carbon atoms in the aryl portion, aryl containing up to 10 carbon atoms, alkenyl, $C_{1-10}$ acyl, alkynyl, or sulphonyl, optionally substituted by $C_{1-10}$ alkyl, aryl containing up to 10 carbon atoms or aralkyl containing 1 to 4 carbon atoms in the alkyl portion and up to 10 carbon atoms in the aryl portion;

Y is $O, S, SO, SO_2, CH_2, CO$ or $NR^7$;

$R^1$ is $COR^8$, $COOR^8$, CHO, $CH_2OH$, $CH_2OR^9$, $CONH_2CONHNR^{10}R^{11}$, $CONHR^{10}$, $CONR^{10}R^{11}$, $COO(CH_2)NR^{10}R^{11}$ wherein $R^8$ is H, $C_{1-10}$ alkyl, aryl containing up to 10 carbon atoms, and optionally substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano or aralkyl containing 1 to 4 carbon atoms in the alkyl portion and up to 10 carbon atoms in the aryl portion, $R^9$ is $C_{1-10}$ acyl optionally substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano, $R^{10}$ and $R^{11}$ are independently hydrogen, $C_{1-10}$ alkyl or aryl containing up to 10 carbon atoms and n is 1 to 4;

$R^2$ is H, $COOR^8$, $C_{1-10}$ alkyl, aryl containing up to 10 carbon atoms and optionally substituted by $C_{1-10}$ alkyl, $C_{1-10}$ alkoxy, halo, sulphinyl, amino (optionally substituted by one or two $C_{1-10}$ alkyl groups), haloalkyl, sulphinyl or cyano or $CH_2CH_2CO_2R^{12}$ wherein $R^{12}$ is $C_{1-10}$ alkyl or aryl containing up to 10 carbon atoms;

$R^3$ and $R^4$ are independently H, hydroxy, $C_{1-10}$ alkyl, haloalkyl, $C_{1-10}$ alkoxy, halo, cyano, nitro, amino, alkylamino, dialkylamino, alkyl substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano, carboxyl or $CO_2R^{12}$;

$R^5$ is H, $C_{1-10}$ alkyl, optionally substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano, aralkyl containing 1 to 4 carbon atoms in the alkyl portion and up to 10 carbon atoms in the aryl portion, nitro, amino, halo, cyano, CHO or $COOR^8$;

$R^6$ is H, $C_{1-10}$ alkyl, aryl containing up to 10 carbon atoms, aralkyl containing 1 to 4 carbon atoms in the alkyl portion and up to 10 carbon atoms in the aryl portion, nitro, halogen, CHO or $COR^{13}$ wherein $R^{13}$ is $C_{1-10}$ alkyl or aryl containing up to 10 carbon atoms with the proviso that (i) when $R^2$, $R^3$, $R^4$, $R^5$ and $R^6$ are all H and A is

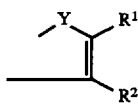

wherein Y is NH and X is O or S, then $R^1$ is not $CO_2H$ or $CO_2Et$;

(ii) when $R^2$, $R^3$, $R^4$, $R^5$ and $R^6$ are all H and A is

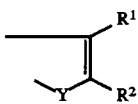

wherein Y is NH, and X is O or S then $R^1$ is not CHO;

(iii) Y is not O when X is O;

(iv) when $R^2$ to $R^6$ are all H, A is

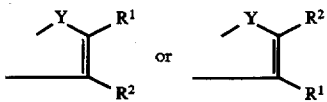

wherein X is S and Y is NH, then $R^1$ is not CHO;

(v) when $R^2$ to $R^6$ are all H, and A is

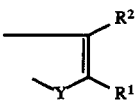

wherein X and Y are both NH, then $R^1$ is not $CO_2H$ or $CO_2Et$;

(vi) when $R^2$ to $R^6$ are all H, and A is

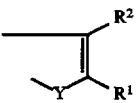

wherein X is $CH_2$ or CO and Y is NH, then $R^1$ is not $CO_2Et$; and (vii) when $R^2$ to $R^6$ are all H, and A is

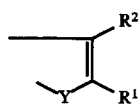

wherein X is S and Y is NH, then $R^1$ is not $CO_2H$ or $CO_2Et$.

2. A compound according to claim 1 in which

X is O, S or $NR^7$, wherein $R^7$ is H, $C_{1-10}$ alkyl, sulphonyl or toluene sulphonyl;

Y is $NR^7$;

$R^1$ is $COR^8$, $COOR^8$, $CH_2OR^9$, $CONH_2$, $CONHNR^{10}R^{11}$, $CONHR^{10}$, $CONR^{10}R^{11}$, $COO(CH_2)_nNR^{10}R^{11}$ wherein $R^8$ is H, $C_{1-10}$ alkyl, aryl containing up to 10 carbon atoms, optionally substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano or aralkyl containing 1 to 4 carbon atoms in the alkyl portion and up to 10 carbon atoms in the aryl portion, $R^9$ is $C_{1-10}$ acyl optionally substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano, $R^{10}$ and $R^{11}$ are independently hydrogen, $C_{1-10}$ alkyl or aryl containing up to 10 carbon atoms and n is 1 to 4 carbon atoms;

$R^2$ is $COOR^8$, $C_{1-10}$ alkyl or $CH_2CH_2CO_2R^{12}$ wherein $R^{12}$ is $C_{1-10}$ alkyl or aryl containing up to 10 carbon atoms;

$R^3$ to $R^4$ are independently H, hydroxy, $C_{1-10}$ alkyl, $C_{1-10}$ alkoxy, halo, cyano, alkyl substituted by $C_{1-10}$ alkyl, $C_{1-10}$ alkoxy, halo, sulphinyl, amino (optionally substituted by one or two $C_{1-10}$ alkyl groups), haloalkyl, sulphonyl or cyano or carboxyl;

$R^5$ is H or $C_{1-10}$ alkyl;

$R^6$ is H, $C_{1-10}$ alkyl or aryl containing up to 10 carbon atoms; and salts and physiologically functional derivatives thereof.

3. A compound according to claim 1 in which

X is S or NH;

Y is NH;

A is

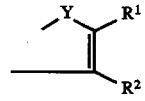

$R^1$ is $COOR^8$ wherein $R^8$ is $C_{1-10}$ alkyl, or aralkyl containing 1 to 4 carbon atoms in the alkyl portion and up to 10 carbon atoms in the aryl portion;

$R^2$ is H or $C_{1-10}$ alkyl;

$R^3$ is H, $C_{1-10}$ alkoxy, or halo;

$R^4$ is H, $C_{1-10}$ alkoxy or halo;

$R^5$ is $C_{1-10}$ alkyl;

$R^6$ is hydrogen;

and salts and physiologically functional derivatives thereof.

4. A compound selected from the group consisting of 3-pyridyl 3,4-dimethylpyrrolo[3,2-b]carbazole-2-carboxylate;

[(3-dimethylamino)phenyl]3,4-dimethylpyrrolo[3,2-b]carbazole-2-carboxylate;

benzyl 1,3,4-trimethylpyrrolo[3,2-b]carbazole-2-carboxylate;

phenyl 3,4-dimethylpyrrolo[3,2-b]carbazole-2-carboxylate;

3,4-dimethyl-2-(1-imidazolylcarbonyl)pyrrolo[3,2-b]carbazole;

ethyl 3,4-dimethylpyrrolo[3,2-b]carbazole-2-carboxylate;

ethyl 3,4-dimethylbenzothieno[4,5-f]indole-2-carboxylate;

benzyl 3,4-dimethylpyrrolo[3,2-b]carbazole-2-carboxylate;

benzyl 8-fluoro-3,4-dimethylpyrrolo[3,2-b]carbazole-2-carboxylate;

ethyl 8-fluoro-3,4-dimethylpyrrolo[3,2-b]carbazole-2-carboxylate;

benzyl 3,4,6-trimethylpyrrolo[3,2-b]carbazole-2-carboxylate;

ethyl 3,4,6-trimethylpyrrolo[3,2-b]carbazole-2-carboxylate;

8-fluoro-3,4-dimethylpyrrolo[3,2-b]carbazole-2-carboxylic acid;

3,4-dimethylpyrrolo[3,2-b]carbazole-2-carboxylic acid;

ethyl 8-methoxy-3,4-dimethylpyrrolo[3,2-b]carbazole-2-carboxylate;

3,4,6-trimethylpyrrolo[3,2-b]carbazole-2-carboxylic acid; and benzyl 8-methoxy-3,4-dimethylpyrrolo[3,2-b]carbazole-2-carboxylate;

and salts and physiologically functional derivatives thereof.

5. A pharmaceutical formulation which comprises a compound of formula (I) according to claim 1 together with a pharmaceutically acceptable carrier thereof.

6. A method of treating susceptible tumors in animals comprising administering to said animal tumor-effective amount of a compound of the formula (I)

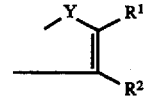

and salts and physiologically function derivative thereof, wherein

A is

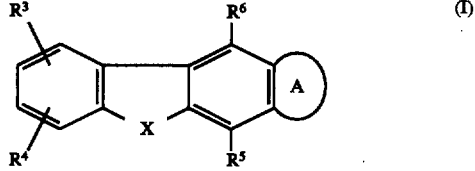

X is O, S, SO, SO$_2$, CH$_2$, CO or NR$^7$, wherein R$^7$ is H, C$_{1-10}$ alkyl, aralkyl containing 1 to 4 carbon atoms in the alkyl portion and up to 10 carbon atoms in the aryl portion, aryl containing up to 10 carbon atoms, alkenyl, C$_{1-10}$ acyl, alkynyl, or sulphonyl, optionally substituted by C$_{1-10}$ alkyl, aryl containing up to 10 carbon atoms or aralkyl containing 1 to 4 carbon atoms in the alkyl portion and up to 10 carbon atoms in the aryl portion;

Y is O, S, SO, SO$_2$, CH$_2$, CO or NR$^7$;

R$^1$ is COR$^8$, COOR$^8$, CHO, CH$_2$OH, CH$_2$OR$^9$, CONH$_2$, CONHNR$^{10}$R$^{11}$, CONHR$^{10}$, CONR$^{10}$R$^{11}$, COO(CH$_2$)$_n$NR$^{10}$R$^{11}$ wherein R$^8$ is H, C$_{1-10}$ alkyl, aryl containing up to 10 carbon atoms and optionally substituted by C$_{1-10}$ alkyl, C$_{1-10}$ alkoxy, halo, sulphinyl, amino, amino substituted by one or two C$_{1-10}$ alkyl groups, haloalkyl, sulphonyl or cyano or aralkyl containing 1 to 4 carbon atoms in the alkyl portion and up to 10 carbon atoms in the aryl portion, R$^9$ is C$_{1-10}$ acyl optionally substituted by C$_{1-10}$ alkyl, C$_{1-10}$ alkoxy, halo, sulphinyl, amino, amino substituted by one or two C$_{1-10}$ alkyl group, haloalkyl, sulphonyl or cyano, R$^{10}$ and R$^{11}$ are independently hydrogen, C$_{1-10}$ alkyl or aryl containing up to 10 carbon atoms and n is 1 to 4;

R$^2$ is H, COOR$^8$, C$_{1-10}$ alkyl, aryl containing up to 10 carbon atoms and optionally substituted by C$_{1-10}$ alkyl, C$_{1-10}$ alkoxy, halo sulphinyl, amino, amino substituted by one or two C$_{1-10}$ alkyl groups, haloalkyl, sulphinyl or cyano or CH$_2$CH$_2$CO$_3$R$^{12}$ wherein R$^{12}$ is C$_{1-10}$ alkyl or aryl containing up to 10 carbon atoms;

R$^3$ and R$^4$ are independently H, hydroxy, C$_{1-10}$ alkyl, haloalkyl C$_{1-10}$ alkoxy, halo cyano, nitro, amino, alkylamino, dialkylamino, alkyl substituted by C$_{1-10}$ alkyl, C$_{1-10}$ alkoxy, halo sulphinyl, amino, amino substituted by one or two C$_{1-10}$ alkyl groups, haloalkyl, sulphonyl or cyano, carboxyl or CO$_2$R$^{12}$;

R$^5$ is H, C$_{1-10}$ alkyl, optionally substituted by C$_{1-10}$ alkyl, C$_{1-10}$ alkoxy, halo, sulphinyl, amino, amino substituted by one or two C$_{1-10}$ alkyl groups, haloalkyl, sulphonyl or cyano, aralkyl containing 1 to 4 carbon atoms in the alkyl portion and up to 10 carbon atoms in the aryl portion, nitro, amino, halo, cyano, CHO or COOR$^8$;

R$^6$ is H, C$_{1-10}$ alkyl, aryl containing up to 10 carbons, aralkyl containing 1 to 4 carbon atoms in the alkyl portion and up to 10 carbon atoms in the aryl portion, nitro, halogen, CHO or COR$^{13}$ wherein R$^{13}$ is C$_{1-10}$ alkyl or aryl containing up to 10 carbon atoms, with the proviso that (i) when R$^2$, R$^3$, R$^4$, R$^5$ and R$^6$ are all H and A is

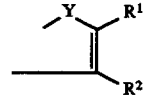

when Y is NH and X is O or S, then R$^1$ is not CO$_2$H or CO$_2$Et;

(ii) when R$^2$, R$^3$, R$^4$, R$^5$ and R$^6$ are all H and A is as defined in proviso (i) above when Y is NH, and X is O then R$^1$ is not CHO;

(iii) Y is not O when X is O; and (iv) when R$^2$, R$^3$, R$^4$, R$^5$ and R$^6$ are all H and A is

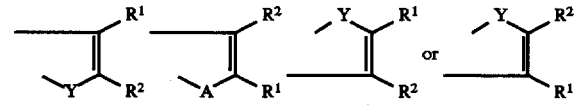

when Y is NH and X is S, then R$^1$ is not CHO.

7. A compound of the formula (IV):

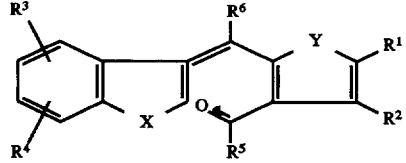

and salts and physiologically functional derivative thereof, wherein

A is

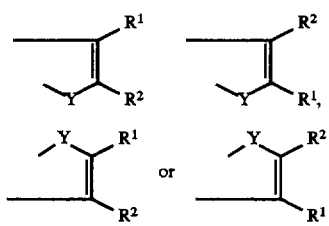

X is O, S, SO, $SO_2$, $CH_2$, CO or $NR^7$, wherein $R^7$ is H, $C_{1-10}$ alkyl, aralkyl containing 1 to 4 carbon atoms in the alkyl portion and up to 10 carbon atoms in the aryl portion, aryl containing up to 10 carbon atoms, alkenyl, $C_{1-10}$ acyl, alkynyl, or sulphonyl, optionally substituted by $C_{1-10}$ alkyl, aryl containing up to 10 carbon atoms or aralkyl containing 1 to 4 carbon atoms in the alkyl portion and up to 10 carbon atoms in the aryl portion;

Y is O, S, SO, $SO_2$, $CH_2$, CO or $NR^7$;

$R^1$ is $COR^8$, $COOR^8$, CHO, $CH_2OH$, $CH_2OR^9$, $CONH_2$, $CONHNR^{10}R^{11}$, $CONHR^{10}$, $CONR^{10}R^{11}$, $COO(CH_2)_nNR^{10}R^{11}$ wherein $R^8$ is H, $C_{1-10}$ alkyl, aryl containing up to 10 carbon atoms and optionally substituted by $C_{1-10}$ alkyl, $C_{1-10}$ alkoxy, halo, sulphinyl, amino, amino substituted by one or two $C_{1-10}$ alkyl group, haloalkyl, sulphonyl or cyano or aralkyl containing 1 to 4 carbon atoms in the alkyl portion and up to 10 carbon atoms in the aryl portion, $R^9$ is $C_{1-10}$ acyl optionally substituted by $C_{1-10}$ alkyl, $C_{1-10}$ alkoxy, halo, sulphinyl, amino, amino substituted by one or two $C_{1-10}$ alkyl group, haloalkyl, sulphonyl or cyano, $R^{10}$ and $R^{11}$ are independently hydrogen, $C_{1-10}$ alkyl or aryl containing up to 10 carbon atoms and n is 1 to 4:

$R^2$ is H, $COOR^8$, $C_{1-10}$ alkyl, aryl containing up to 10 carbon atoms and optionally substituted by $C_{1-10}$ alkyl, $C_{1-10}$ alkoxy, halo sulphinyl, amino, amino substituted by one or two $C_{1-10}$ alkyl groups, haloalkyl, sulphinyl or cyano or $CH_2CH_2CO_3R^{12}$ wherein $R^{12}$ is $C_{1-10}$ alkyl or aryl containing up to 10 carbon atoms;

$R^3$ and $R^4$ are independently H, hydroxy, $C_{1-10}$ alkyl, haloalkyl $C_{1-10}$ alkoxy, halo cyano, nitro, amino, alkylamino, dialkylamino, alkyl substituted by $C_{1-10}$ alkyl, $C_{1-10}$ alkoxy, halo sulphinyl, amino, amino substituted by one or two $C_{1-10}$ alkyl groups, haloalkyl, sulphinyl or cyano, carboxyl or $CO_2R^{12}$;

$R^5$ is H, $C_{1-10}$ alkyl, optionally substituted by $C_{1-10}$ alkyl, $C_{1-10}$ alkoxy, halo, sulphinyl, amino, amino substituted by one or two $C_{1-10}$ alkyl groups, haloalkyl, sulphonyl or cyano aralkyl containing 1 to 4 carbon atoms in the alkyl portion and up to 10 carbon atoms in the aryl portion, nitro, amino, halo, cyano, CHO or $COOR^8$;

$R^6$ is H, $C_{1-10}$ alkyl, aryl containing up to 10 carbons, aralkyl containing 1 to 4 carbon atoms in the alkyl portion and up to 10 carbon atoms in the aryl portion, nitro, halogen, CHO or $COR^{13}$ wherein $R^{13}$ is $C_{1-10}$ alkyl or aryl containing up to 10 carbon atoms, with the proviso that (i) when $R^2$, $R^3$, $R^4$, $R^5$ and $R^6$ are all H and A is

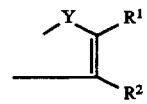

when Y is NH and X is O or S, then $R^1$ is not $CO_2H$ or $CO_2Et$;

(ii) when $R^2$, $R^3$, $R^4$, $R^5$ and $R^6$ are all H and A is as defined in proviso (i) above when Y is NH, and X is O then $R^1$ is not CHO;

(iii) Y is not O when X is O; and (iv) when $R^2$, $R^3$, $R^4$, $R^5$ and $R^6$ are all H and A is

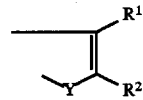

when Y is NH and X is S, then $R^1$ is not CHO.

* * * * *